US006274603B1

(12) United States Patent
Poirier

(10) Patent No.: US 6,274,603 B1
(45) Date of Patent: Aug. 14, 2001

(54) METHODS FOR INCREASING APOE LEVELS FOR THE TREATMENT OF NEURODEGENERATIVE DISEASE

(75) Inventor: Judes Poirier, Boisbriand (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/160,462

(22) Filed: Sep. 24, 1998

Related U.S. Application Data

(60) Provisional application No. 60/059,908, filed on Sep. 24, 1997.

(51) Int. Cl.[7] ......................... A61K 31/445; A61K 31/35
(52) U.S. Cl. ............................................ 514/330; 514/451
(58) Field of Search ................... 514/330, 451; 548/429

(56) References Cited

U.S. PATENT DOCUMENTS

| 4,831,155 | * | 5/1989 | Brufani et al. | 548/429 |
|---|---|---|---|---|
| 5,554,601 | * | 9/1996 | Simpkins et al. | 514/182 |
| 5,668,117 | | 9/1997 | Shapiro | 514/55 |

FOREIGN PATENT DOCUMENTS

| 0 296 560 | 12/1988 | (EP) | C07D/211/26 |
|---|---|---|---|
| WO 95 01096 | 1/1995 | (WO) | A01N/43/04 |
| WO 95 06470 | 3/1995 | (WO) | A61K/31/435 |
| WO 95 29257 | 11/1995 | (WO) | C12Q/1/68 |
| WO 96/30012 | 10/1996 | (WO) | A61K/31/375 |
| WO 97 38694 | 10/1997 | (WO) | A61K/31/53 |
| WO 97 46526 | 12/1997 | (WO) | C07D/211/32 |
| WO 98 31366 | 7/1998 | (WO) | A61K/31/445 |
| WO 98 51289 | 11/1998 | (WO) | A61K/31/00 |

OTHER PUBLICATIONS

Gutman et al., "Apolipoprotein E Binds to and Potentiates the Biological Activity of Ciliary Neurotrophic Factor," *The Journal of Neuroscience* 17:6114–6121 (1997).
Aburatani et al., Amer. J. Cardiology 62:605–655 (Jul. 1988).
Buckley et al., Drugs 37:761–800 (1989).
Carr et al., Contraception 55:267–272 (1997).
Connolly et al., Neurosurgery 38:523–531 (Mar. 1996).
Eto et al., Atherosclerosis 84:49–53 (1990).
Fujimura et al., European Journal of Clincal Pharmacology 43:299–301 (1992).
Grodstein et al., New Eng. J. Med. 335:453–461 (Aug. 1996).
Heeg et al., Journal of Pharmaceutical Sciences 73:1758–1763 (Dec. 1984).
Heineke et al., Diabetes 42:1721–1730 (Dec. 1993).
Komura et al., European Journal of Drug Metabolism & Pharmacokinetics 22:201–206 (1997).
Kondo et al., Neurosci. Lett. 238: 45–48 (1997).
Mantha et al., Life Sci. 58:503–509 (1996).
Mao et al., J. Med. Chem. 34:298–302 (1991).
Nawashiro et al., J. Cereb. Blood Flow Metab. 17:483–490 (1997).
Nestruck et al., Metabolism 36:743–747 (Aug. 1987).
Nourooz–Zadeh et al., J. Chromatography 654:55–60 (1994).
Neuworth et al., J. of Medicinal Chemistry 13:722–725 (1970).
Pettitti et al., Stroke 29:23–28 (1998).
Pettitti et al., New Eng. J. Med. 335:8–15 (Jul. 1996).
Poirier et al., Neuroscience 55:81–90 (1993).
Reaven et al., Arterioscler. Thromb. 12:318–324 (Mar. 1992).
Rosenberg et al., Amer. J. Obstetrics & Gynecol. 177:707–715 (1997).
Schneider et al., Ann. NY Acad. Sci. 826:317–322 (1997).
Simpkins et al., J. Neurosurgery 87:724–730 (Nov. 1997).
Srivastava et al., J. Biol. Chem. 272:33360–33366 (Dec. 1997).
Stone et al., J. Neuroscience 18:3180–3185 (1998).
Stone et al., Exp. Neurol. 143:313–318 (1997).
Toung et al., Stroke 29:1666–1670 (1998).
Yamamoto et al., Avzneimittel–Forschung 44:1059–1062 (1994).
Zamorski, J. Family Practice 43:343–344 (Oct. 1996).
Pike et al., "β–Amyloid Neurotoxicity In Vitro: Evidence of Oxidative Stress but Not Protection by Antioxidants," Journal of Neurochemistry 69(4):1601–1611 (1997).
Miettinen et al., "Multifactorial Primary Prevention of Cardiovascular Diseases in Middle–aged Men," JAMA 254:2097–2102 (Oct. 1985).
Stein, "Free Radicals and Antioxidants," Rev bras Neurol. 30(1):12S–17S (1994).
Naito et al., "Protective Effects of probucol against glutamate–induced cytotoxicity in neuronal cell line PC12," Neuroscience Letters 186;211–213 (1995).
Sloininen et al., "Apolipoprotein E, Memory and Alzheimer's disease," TINS 19(6):224–228 (1996).
Kalra et al., "Lewy Body Disease and Dementia," Arch Intern Med 156:487–493 (Mar. 1996).
Kuzuya et al., "Probucol as an antioxidant and antiatherogenic drug" *Free Radical Biology & Medicine* 14:67–77 (1993).
McPherson et al., "Time course changes in plasma concentrations of cholesteryl ester transfer protein (CETP), apoprotein E (Apo E), and high density lipoproteins (HDL) during probucol treatment in man" *Arteriosclerrosis* 10(5):818a (Sep. 10, 1990).

* cited by examiner

*Primary Examiner*—Marianne P. Allen
*Assistant Examiner*—Marjorie A. Moran
(74) *Attorney, Agent, or Firm*—Clark & Elbing LLP

(57) ABSTRACT

Disclosed herein is a method for reducing neurodegenerative disease in patients by administration of a therapeutically-effective amount of a compound which can increase ApoE levels.

16 Claims, 14 Drawing Sheets

METHODS FOR INCREASING APOE LEVELS FOR THE TREATMENT OF NEURODEGENERATIVE DISEASE

CROSS-REFERENCE TO RELATED APPLICATION

This application claims benefit from provisional application 60/059,908 filed on Sep. 24, 1997.

BACKGROUND OF THE INVENTION

This invention relates to methods for the treatment of neurodegenerative disease.

Neurodegenerative diseases include Alzheimer's disease (AD) Creutzfeldt-Jakob disease, Huntington's disease, Lewy body disease, Pick's disease, Parkinson's disease, amyotrophic lateral sclerosis (ALS), neurofibromatosis, and diseases without a necessary genetic component such as brain injury, stroke, and multiple infarct dementia. Most of these diseases are typified by onset during the middle adult years and lead to rapid degeneration of specific subsets of neurons within the neural system, ultimately resulting in premature death. There are no known cures and few therapies that slow the progression of these diseases.

Alzheimer's disease (AD) is one of the most clinically important of the neurodegenerative diseases due to the high frequency of occurrence within the population and the fatal course of the disease. Two forms of the disease exist: presenile dementia, in which the symptoms emerge during middle age, and senile dementia which occurs in the elderly. Both forms of the disease appear to have the same pathology. A clear genetic predisposition has been found for presenile dementia. Familial autosomal dominant cases have been reported and the majority of individuals with trisomy 21 (Down's syndrome) develop presenile dementia after the age of 40. The genetic loci associated with familial Alzheimer's disease map to chromosomes 14, 19, and 21, with more than one locus on 21.

Pick's disease (lobar sclerosis) is expressed clinically as dementia that is essentially indistinguishable from that of Alzheimer's disease. The disease becomes symptomatic in middle adulthood and progresses relentlessly over a period of 3 to 5 years. Some of Pick's disease cases cluster in families, but the case distributions do not conform to a strictly hereditary pattern. Women are affected by the disease more often than men.

The brain in Pick's disease is atrophic. Unlike Alzheimer's disease, the atrophy is typically localized in a frontal or a temporal lobe, and it may attain extreme proportions. Histologically, the involved cortex is markedly depleted of neurons, and their absence is accentuated by a marked astrogliosis. Many residual neurons have a "ballooned" cytoplasm, and in some, there is one or more faintly eosinophilic inclusions, termed Pick bodies, whose presence is confirmed by their intense argentophilia. These bodies are formed of densely aggregated neurofilaments.

Creutzfeldt-Jakob disease was named after the two doctors from Austria who in 1920 separately described a total of six patients with peculiar neurological illnesses. Although the illnesses were not very similar, the post mortem brain tissue appeared similar when viewed under the microscope. Many of the normal brain nerve cells were dead and the tissue had numerous tiny holes, resembling a sponge, hence, the expression "spongiform encephalopathy" is also used to describe the disease.

Creutzfeldt-Jakob disease (CJD) occurs worldwide. There is approximately one new case per two million people per year with the age of onset occurring between the ages of 55 and 80. CJD can affect more than one member of a family but this is rare.

Huntington's disease is a progressive disease which is always transmitted as an autosomal dominant trait mapping to a single locus on chromosome 4. Individuals are generally asymptomatic until the middle adult years, although some patients show symptoms as early as age 15. Once symptoms appear, the disease is characterized by choreoathetotic movements and progressive dementia until death 15–20 years after the age of onset.

Autopsies of Huntington's disease patients reveal progressive atrophy of the caudate nucleus and basal ganglia. Atrophy of the caudate nucleus and the putamen is seen microscopically where there is an excessive loss of neural tissue.

Although some of the characteristic mental depression and motor symptoms associated with Huntington's may be suppressed using tricyclic antidepressants and dopamine receptor antagonists, respectively, no therapy exists for slowing or preventing the underlying disease process Parkinson's disease is a common neurodegenerative disorder which first appears in mid to late life. Familial and sporadic cases occur, although familial cases account for only 1–2 percent of the observed cases. The neurological changes which cause this disease are somewhat variable and not fully understood. Patients frequently have nerve cell loss with reactive gliosis and Lewy bodies in the substantia nigra and locus coeruleus of the brain stem. Similar changes are observed in the nucleus basalis of Meynert. As a class, the nigrostriatal dopaminergic neurons seem to be most affected.

The disorder generally develops asymmetrically with tremors in one hand or leg and progresses into symmetrical loss of voluntary movement. Eventually, the patient becomes incapacitated by rigidity and tremors. In the advanced stages the disease is frequently accompanied by dementia.

Diagnosis of both familial and sporadic cases of Parkinson's disease can only be made after the onset of the disease symptoms. Anticholinergic compounds, such as propranolol, primidone, and levodopa, are frequently administered to modify neural transmissions and thereby suppress the symptoms of the disease, though there is no known therapy which halts or slows the underlying progression.

Lewy body disease is a preferred term which describes several common disorders causing dementia. In many hospitals this is the second most common * cause of dementia following Alzheimer's disease. The name for the disease comes from the presence of abnormal lumps called Lewy bodies which develop inside nerve cells.

The primary clinical symptom of this condition is the development of dementia, although patients may also show Parkinsonian symptoms and experience hallucinations.

Autopsy of Lewy body disease patients reveals degeneration of the substantia nigra, as would be seen in Parkinson's disease. In Lewy body dementia and Parkinson's disease, the melanin containing nerve cells of the substantia nigra die and the tissue thus appears abnormally pale in comparison to normal tissue. The cause of Lewy body disease is uncertain. However, an association with a higher apoE4 allele frequency has been noted.

Neurofibromatosis actually refers to at least two related but quite distinct diseases.

Neurofibromatosis 1 (NF1, peripheral neurofibromatosis, von Recklinghausen disease) is characterized by multiple neurofibromas, cafe au lait macules, and Lisch nodules of the iris. Some patients with NF1 also show learning disabilities, macrocephaly, bony abnormalities, and a higher frequency of neural malignancies.

Neurofibromatosis 2 (NF2, central neurofibromatosis) is characterized by the appearance of bilateral vestibular schwannomas. The majority of NF2 patients develop schwannomas of cranial or peripheral nerves while a minority develop other tumors, such as meningiomas and ependymomas.

Both NF1 and NF2 are autosomal dominant disorders with nearly full penetrance and occur spontaneously 50% of the time. NF1, with an incidence of 1 in 40,000 individuals is a much more rare disorder then NF2, which has an incidence of 1 in 3,000.

Reflective of their very different clinical appearances, NF1 and NF2 are caused by two entirely different genes. The NF1 gene on chromosome 17 encodes a protein named neurofibromin. The function of neurofibromin is unclear, although it does contain a single domain with GTPase activating activity. The NF2 gene on chromosome 22 encodes the Merlin protein. The exact function of Merlin is also unknown, but it is highly homologous to a family of cytoskeleton associated proteins including moesin, ezrin, radixin, and talin.

Amyotrophic lateral sclerosis (ALS) is the most commonly diagnosed progressive motor neuron disease. The disease is characterized by degeneration of motor neurons in the cortex, brainstem, and spinal cord. Generally, the onset is between the third and sixth decade. ALS is uniformly fatal, typically within five years. The cause of the disease is unknown although some cases of familial ALS map to the sod-1 gene.

Post mortem brains from ALS patients show affected neurons of the cerebral cortex, the anterior horns of the spinal cord, and the homologues in some of the motor nuclei of the brain stem. The class of neurons affected is highly specific: first motor neurons for ocular motility, then later in the disease, sphincteric motor neurons of the spinal cord.

Although death occasionally results shortly after the onset of this symptomatic disease, the disease generally ends with respiratory failure secondary to profound generalized and diaphragmatic weakness.

Multiple Sclerosis (MS) is a neurodegenerative disease of the brain and spinal cord in which a breakdown occurs in the myelin sheathing of the nerve fibers. MS is currently incurable and treatments are few and usually result in only temporary improvements of the disease symptoms.

Brain injury, stroke, and multiple infarct dementia are injuries to the brain that have no necessary genetic component but often result in similar neuronal deficits similar to those seen in the genetic disorders described above.

Apolipoprotein E (ApoE) has been extensively studied in non-nervous tissues as one of several proteins that regulate lipid metabolism and transport. ApoE facilitates cholesterol transport between different cell types and different organs. Specifically, it binds to large lipid-protein particles (called lipoproteins) and increases their ability to transport cholesteryl esters.

The mature form of ApoE, found in human plasma and cerebrospinal fluid (CSF), is a single, glycosylated, 37 kDa polypeptide containing 299 amino acids. There is some evidence that ApoE may coordinate the mobilization and redistribution of cholesterol in repair, growth, and maintenance of myelin and neuronal membranes during development or after sciatic nerve injury. In the brain, ApoE appears to coordinate the redistribution of cholesterol and phospholipids. Removal of the apoE gene by gene disruption or "knockout," appears to cause some age-dependent reduction of synaptic contacts in the cortex and impairment of reinnervation in the hippocampus.

In humans there are three major isoforms of ApoE (E4, E3 and E2) differing by a single unit of net charge which can be easily detected by isoelectrofocusing. These isofonns are expressed from multiple alleles at a single apoE genetic locus, giving rise to three common homozygous phenotypes (E4/4, E3/3 and E2/2) and three common heterozygous phenotypes (E4/3, E4/2, and E3/2).

The allele frequency of apoE4 is markedly increased in sporadic and late onset familial Alzheimer's disease (AD). As many as 80% of clinical cases of AD (aged between 65 and 75 years) carry the E4 allele compared to only 15% in the normal population.

Drugs for the treatment of patients with neurodegenerative disease, such as Alzheimer's disease, are few in number despite the need for such therapies. Only two FDA approved drugs are currently approved for treating symptoms of Alzheimer's disease: tacrine (Cognex™ manufactured by Parke-Davis) and donepezil (Ariceptf marketed by Pfizer).

SUMMARY OF THE INVENTION

In general, the invention features a method of preventing a neuronal deficit in a patient diagnosed with a neurological disease or predisposition to a neurological disease. The method includes administering to the patient a therapeutically-effective amount of a composition capable of increasing ApoE levels. Preferably the compound is one of the following: probucol, tacrine, heptylphysostignine, simvastatin, lovastatin, pravastatin, thorvastatin, probucol analogs, vitamin E, donepezil, blood pressure inhibitors, antioxidants, anti-inflammatories, and steroids. Use of tacrine, donepezil, or estrogen alone for the treatment of Alzheimer's disease is specifically excluded. In one embodiment, AD and stroke are specifically excluded from the neurological diseases of the invention. Methods for the treatment of Alzheimer's disease with tacrine, donepezil, or estrogen includes administering another compound such as a second ApoE enhancing compound or vitamin E. The therapeutically-effective amount of the composition used in the methods is a dosage which is sufficient to increase ApoE levels in the patient being treated. Further, in one embodiment the increase in ApoE levels is sufficient to also increase amyloid scavenging.

In preferred embodiments, the patient has been identified as having at least one apoE4 allele; the patient has afflictions that affect either the central nervous system (CNS), peripheral nervous system (PNS), or both; the patient has been diagnosed to suffer from, or have a genetic predisposition to, a neurodegenerative disease such as Alzheimer's disease, Creutzfeldt-Jakob disease, Huntington's disease, Lewy body disease, Parkinson's disease, Pick's disease, amyotrophic lateral sclerosis, multiple sclerosis, neurofibromatosis, stroke, multiple infarct dementia, or brain injury.

In other embodiments, the invention provides a method for treating presymptomatic as well as symptomatic patients and the method may include a preferred dosage administered orally but also may include other drug delivery methods known to those skilled in the art.

The invention also provides a method for increasing ApoE levels in a patient by administering a therapeutically-effective amount of a composition selected from the group comprising probucol, tacrine, heptylphysostigmine, simvastatin, lovastatin, pravastatin, thorvastatin, probucol analogs, vitamin E, donepezil, blood pressure inhibitors, antioxidants, anti-inflammatories, and steroids. The increase in ApoE levels may be measured by quantitating ApoE polypeptide with an antibody or by other methods known to those skilled in the art for quantitating increases in biological activity, gene expression, or protein levels. In various preferred embodiments, the patient has at least one apoE4 allele; is suffering from or is genetically predisposed to suffer from a disease selected from the group consisting of Alzieimer's disease, Creutzfeldt-Jakob disease, Huntington's disease, Parkinson's disease, Pick's disease, Lewy body disease, amyotrophic lateral sclerosis, multiple sclerosis, and neurofibromatosis, or a disease without a necessary genetic component such as brain injury, stroke, and multiple infarct dementia. The administration of the compounds for this purpose may be to enhance cognitive performance in both diseased and undiseased individuals.

In another aspect, the invention provides a method for identifying a therapeutic compound effective for the treatment of neurodegenerative disease by exposing a cell, for example an astrocyte, to a compound (or mixture of compounds) and measuring the expression of the apoE gene (e.g., by mRNA or polypeptide quantitation techniques) or, an increase in ApoE polypeptide levels. An increase in one of the above indices indicates a potential therapeutic compound. In a preferred embodiment, the method for identifying a therapeutic compound includes exposing a cell from the nervous system (for example, an astrocyte, an oligodendrocyte, a neuron, or a glial cell) to a compound and measuring the expression of apoE. The cell may be adapted to cell culture or the cell may be derived from a patient afflicted with a neurodegenerative disease (for example, Alzheimer's disease, Creutzfeldt-Jakob disease, Huntington's disease, Parkinson's disease, Pick's disease, Lewy body disease, amyotrophic lateral sclerosis, multiple sclerosis, neurofibromatosis, brain injury, stroke, or multiple infarct dementia). An increase in apoE or ApoE levels is indicative of a therapeutically-effective compound. Preferably, the increase is about 10% or more.

For the purpose of the present invention the following terms are defined below.

By "Alzheimer's Disease (AD)" is meant a pathology characterized by an early and extensive loss of enterhinal cortex neurons. AD patients may be identified by progressive and degenerative effects on the brain which are not attributable to other causes. A diagnosis of Alzheimer's disease is made using clinical-neuropathological correlations known in the art (see, e.g., *Arch. Neurology*, 51(9):888–896 (1994)). Post mortem, the disease may be diagnosed by the presence of amyloid plaques in the brain.

By "non-AD neurological disease (non-AD)" is meant any disease other than Alzheimer's disease, which involves the neuronal cells of the nervous system. Specifically included are: prion diseases (e.g, Creutzfeldt-Jakob disease); pathologies of the developing brain (e.g., congenital defects in amino acid metabolism, such as argininosuccinicaciduria, cystathioninuria, histidinemia, homocystinuria, hyperammonemia, phenylketonuria, and tyrosinemia, and fragile X syndrome); pathologies of the mature brain (e.g., neurofibromatosis, Huntington's disease, depression, amyotrophic lateral sclerosis, multiple sclerosis, and stroke); conditions that strike in adulthood (e.g. Alzheimer's disease, Creutzfeldt-Jakob disease, Huntington's disease, Lewy body disease, Parkinson's disease, Pick's disease, amyotrophic lateral sclerosis, multiple sclerosis, neurofibromatosis, brain injury, stroke, and multiple infarct dementia); and pathologies of the brain (e.g., brain mishaps, brain injury, coma, infections by various agents, dietary deficiencies, and cardiovascular accidents).

By "diagnosed to suffer from a neurological disease" is meant already diagnosed as having the neurological disease, having a genetic predisposition to the disease, or both.

By "genetically predisposed to suffer from a neurological disease" is meant having a genetic predisposition to the disease, for example, as determined by genotyping.

By "apoE allele load" is meant a determination of the type and number of apoE alleles present in the patient, whether determined by nucleic acid sequencing, examination of ApoE protein, or other methods available to those skilled in the art.

By "neuronal deficit" is meant shortage or compromise of any of the conducting cells, support cells, or insulating cells of the central or peripheral nervous system. This term may also refer to altered cognitive aspects such as memory performance, verbal memory, spatial memory, factual memory, or learning capacity. This term may also be used to refer to compromised non-cognitive aspects of the nervous system, for example, motor coordination, voluntary or involuntary neuronal responses, muscle movements or reflexes.

By "treating" is meant the medical management of a patient with the intent to cure, ameliorate, or prevent a disease, pathological condition, or disorder. This term includes active treatment, that is, treatment directed specifically toward the improvement or associated with the cure of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventive treatment, that is, treatment directed to prevention of the associated disease, pathological condition, or disorder; and supportive treatment, that is, treatment employed to supplement another specific therapy directed toward the improvement of the associated disease, pathological condition, or disorder. The term "treating" also includes symptomatic treatment, that is, treatment directed toward constitutional symptoms of the associated disease, pathological condition, or disorder.

By "therapeutically-effective amount" is meant an amount of a pharmaceutical composition sufficient to produce a healing, curative, or ameliorative effect either in the treatment of a neurological disease or in the prevention of a neurological disease.

By "probucol-containing composition" is meant any composition that includes, as a component, probucol.

By "tacrine-containing composition" is meant any composition that includes, as a component, tacrine.

By "therapeutically-effective" is meant that a compound shall increase ApoE protein, as measured as secreted protein circulating in the cerebrospinal fluid, by a measurable amount, as compared to age and disease matched control patients.

By "amyloid scavenging" is meant that a therapeutically effective compound shall increase the amount of amyloid degradation, uptake, or clearance such that the amount of amyloid material is reduced.

The present invention provides two important advantages. First, it provides a therapy for prophylactically halting or reducing neurodegeneration in a patient predisposed to acquire a neurodegenerative condition and, second, the invention can reverse, halt, or slow the progression of a diagnosed disease. Further, the probucol-containing compounds utilized herein are non-toxic, pharmocokinetically well understood, and are known to be well tolerated by mammals. Finally, probucol has the advantage of directly saving and restoring the health of a neural tissue rather than being a mere palliative.

DETAILED DESCRIPTION OF THE INVENTION

The drawings will first be described.

Figure 1:
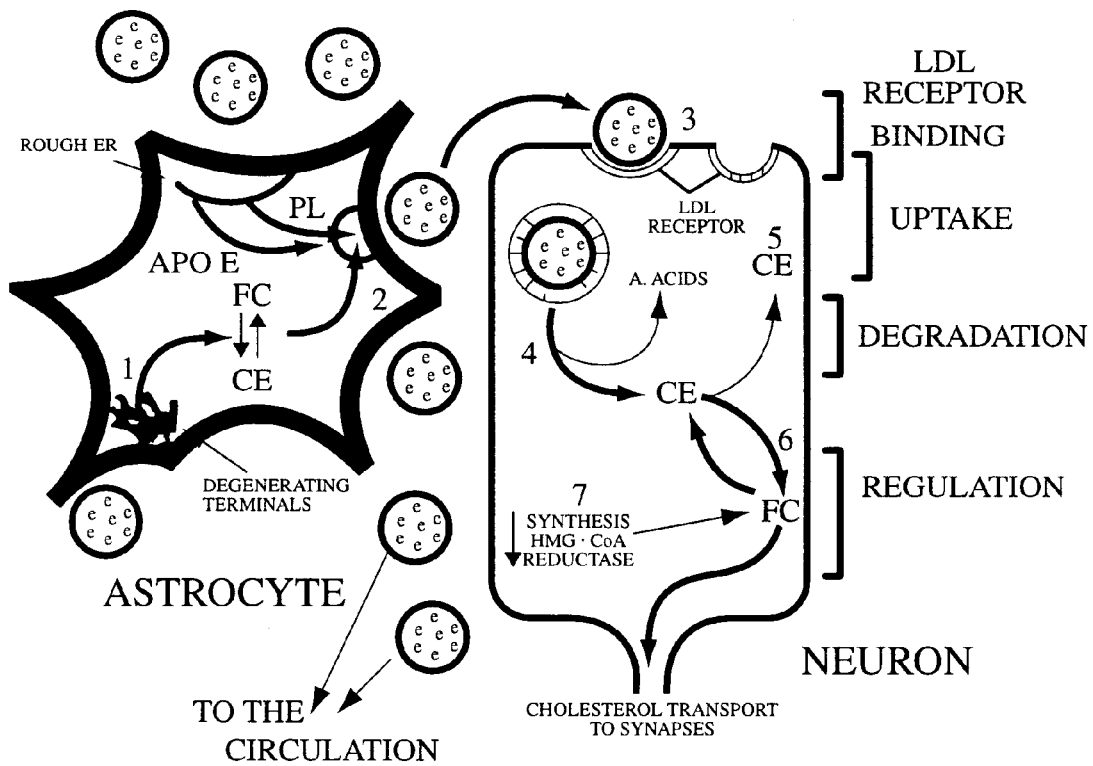
FIG. 1 is a schematic representation of the postulated cascade of events regulating cholesterol transport during CNS reinnervation (FC: free cholesterol; CE: cholesterol esters; and E: ApoE).

The invention described herein features a method for promoting neuroregeneration and repair.

The invention is based on our discovery that some neurodegenerative diseases are related, in part, to abnormal ApoE biology.

Certain apoE alleles, such as the apoE4 allele, encode unstable ApoE gene products that compromise nerve biology. This eventually results in a nervous system deficit or exacerbates a nervous system disease as evidenced by impaired cognitive, sensory, or motor function. We have made an important connection between the molecular pathway within which ApoE works, nerve repair, and how drugs that affect ApoE levels will improve neurological disease symptoms. We propose that a selective dysfunction of the lipid transport system controlled by ApoE could be central to the pathophysiological process that characterizes ApoE4 carrying AD subjects. In addition, we have discovered that increasing ApoE levels improves amyloid scavenging and this may explain observed improvements in animals treated with compounds that can raise ApoE levels. We have conceived of a way to increase ApoE levels using existing drugs, such as probucol and tacrine. We propose that upregulating ApoE levels in AD patients may improve neuroregeneration and this is supported by our observations that both probucol and tacrine increase ApoE levels. Thus, our invention provides a way to directly rescue dying cells of the nervous system by replenishing unstable ApoE protein or enhancing ApoE levels by inducing apoe gene expression by administration of these drugs. The invention further provides for the use of probucol, tacrine, and other ApoE elevating compounds to treat AD and non-AD neurodegenerative disease.

Therefore, as described herein, probucol has important therapeutic properties. Probucol is predicted to improve brain ApoE expression for all patients and to have especially therapeutic effects in patients with genotypes predictive of very low or unstable ApoE expression (e.g., patients having apoE 4/3 and 4/4 allele loads). We predict that other drugs such as heptylphysostigmine, simvastatin, lovastatin, pravastatin, thorvastatin, probucol analogs, vitamin E, donepezil, blood pressure inhibitors, antioxidants, anti-inflammatories, and steroids, will alter ApoE levels and have similar therapeutic health benefits. We also provide methods for readily determining the therapeutic effectiveness of such compounds for use in the methods of the invention.

In addition, the results described herein demonstrate that symptoms of neurodegenerative disease may be exacerbated by low ApoE levels in the brain and that these symptoms will be reduced by increases in ApoE levels. Symptoms of AD and non-AD patients correlate with alterations in ApoE levels and are improved with probucol. The improvement is similar to that observed in AD patients treated with tacrine. The present invention therefore provides methods and reagents for the treatment of AD and non-AD diseases, such as Creutzfeldt-Jakob disease, Huntington's disease, Lewy body disease, Parkinson's disease, Pick's disease, amyotrophic lateral sclerosis, neurofibromatosis, brain injury, stroke, multiple sclerosis, and multiple infarct dementia.

Below we provide experimental data showing the ability of the drugs provided above to increase ApoE expression in cells of the nervous system. Further, our invention provides a clinical trial to demonstrate that patients with a neurodegenerative disease can be effectively treated with these drugs.

Introduction

Eukaryotic cells obtain their cholesterol from two distinct sources: a) it is synthesized directly from acetyl-CoA through the HMG-CoA reductase pathway or, b) it is imported through the apoE/apoB (LDL) receptor family via lipoprotein-complex internalization. These two different pathways are tightly coupled: i.e., a reduced internalization of cholesterol through the receptor pathway will cause increases in HMG-CoA reductase activity (cholesterol synthesis) whereas inhibition of intracellular cholesterol synthesis will induce expression of the LDL receptor and lipoprotein internalization.

Figure 3:
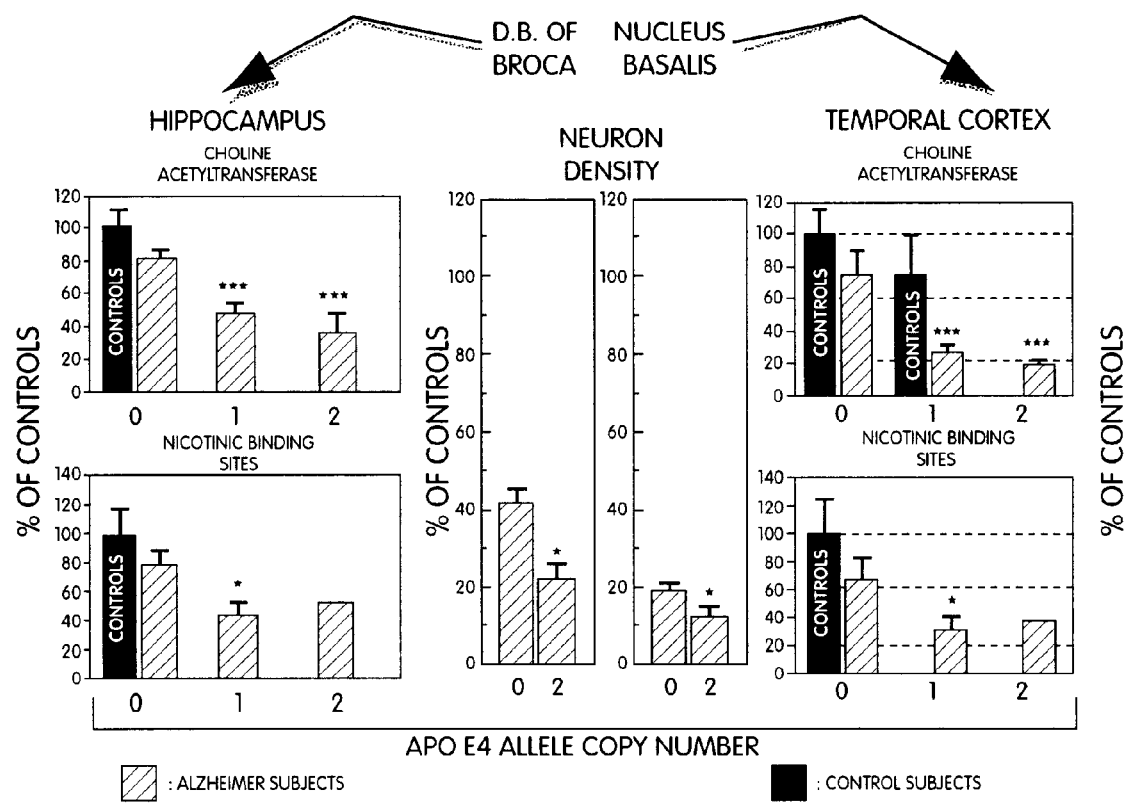
FIG. 3 is a histogram depicting the cholinergic status in the brains of control (solid bars) and Alzheimer's disease subjects (hashed bars) with different apoE genotypes (*:$p<0.05$; * * *:$p<0.001$).
Figure 4:
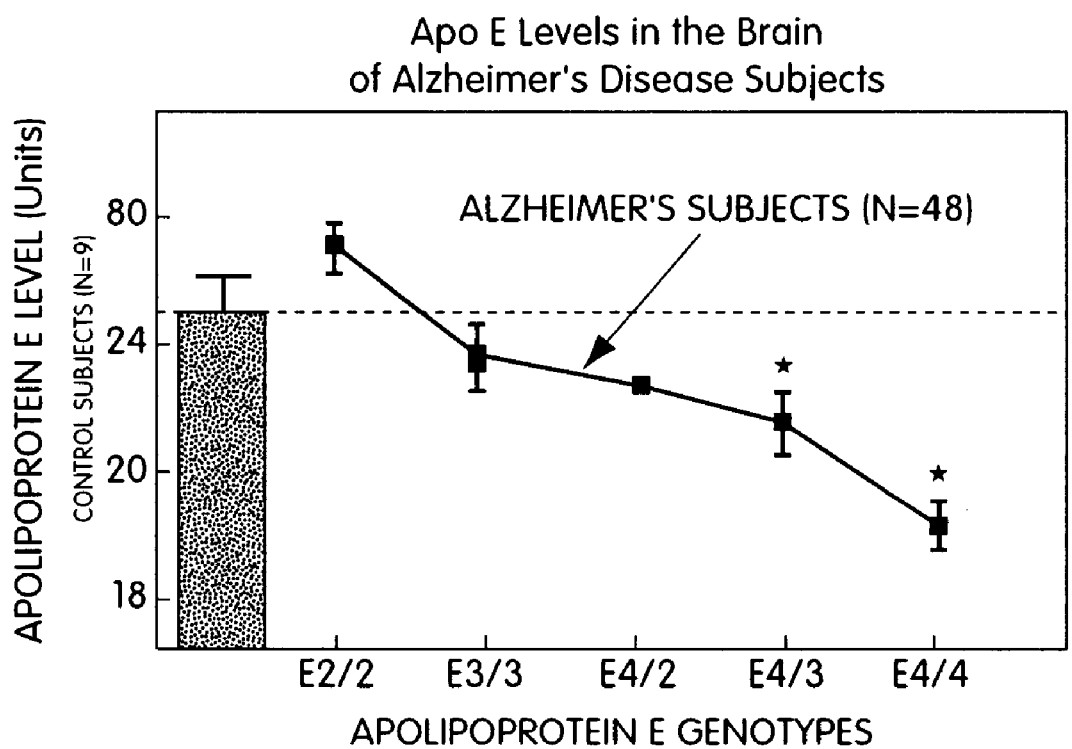
FIG. 4 is a graph depicting brain ApoE levels in Alzheimer's Disease (AD) subjects as a finction of the apoe genotype (*:$p<0.05$ versus apoE3/3 AD subjects). Mean age-matched control value is represented by the solid bar (±SEM).
Figure 7:
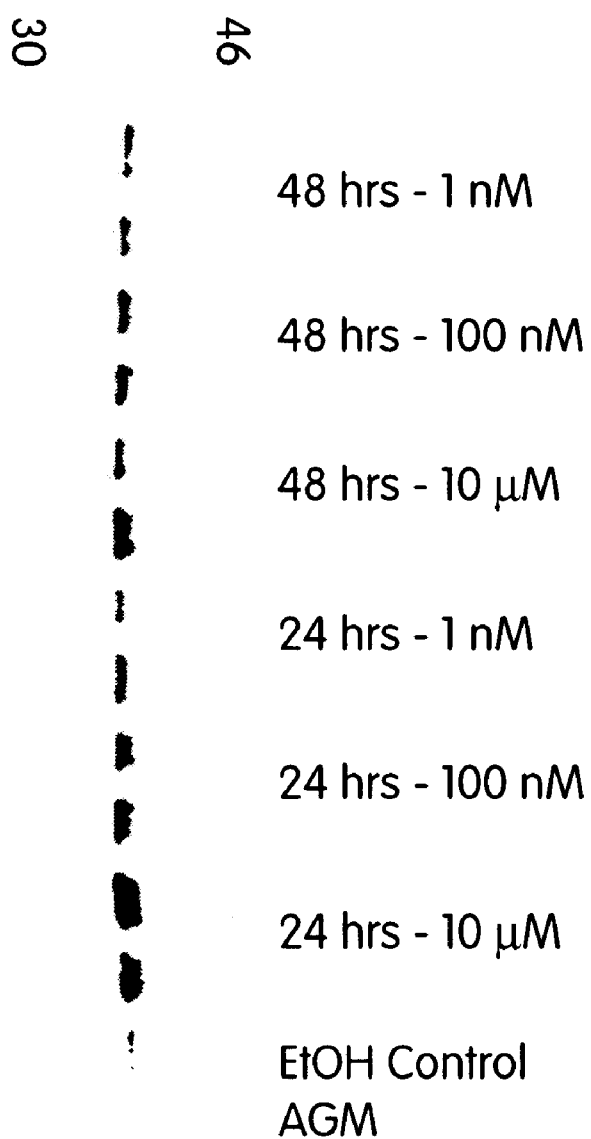
FIG. 7 is a inununoblot showing the effect of different doses of probucol on ApoE secretion and steady state levels in the media of in vitro cultured rat type 1 astrocytes.

Much of the free cholesterol generated during synapse degradation is stored in astrocytes in the central nervous system (CNS) and, in macrophages in the peripheral nervous system (PNS) where it is eventually reused during PNS regeneration and CNS reinnervation. Following binding of the ApoE complexes with neuronal LDL receptors, the ApoE/cholesterol/LDL receptor complex is internalized, degraded and the cholesterol released inside neurons is used for membrane synthesis as well as synaptic remodeling (FIGS. 1, 3, and 4). The increase in intracellular neuronal cholesterol levels causes a down-regulation of HMG-CoA reductase activity and mRNA prevalence in granule cell neurons undergoing dendritic and synaptic remodeling (FIGS. 1 and 7). Following neuronal cell loss and terminal deafferentation in the brain, large amounts of lipids are released from degenerating axon membranes and myelin (FIG. 1, Step 1). In response, astrocytes (FIG. 1, Step 2) and macrophages synthesize and release ApoE within the lesion to scavenge cholesterol from both cellular and myelin debris. Using the activity of the 3,3-hydroxymethylglutaryl-CoA reductase (HMG-COA reductase) to monitor cholesterol synthesis, it was found that a critical phase of cholesterol synthesis is progressively repressed in response to the increase in intracellular cholesterol concentration. Thus, cholesterol required for membrane synthesis can reach critically low levels during periods of neuronal cell injury. Our discovery shows that increases in ApoE synthesis can address this shortage.

The ApoE Link to Non-AD Diseases

We believe that AD patients who are apoE4 carriers are characterized by a defective system of repair due to lower ApoE brain levels. Accordingly, drugs like tacrine and more importantly, probucol, could be used to increase ApoE levels in the brain of apoE4 carriers, improve lipid transport and delivery, and stimulate reinnervation and synapse replacement generally. We believe that it is possible to either stop or slow down the disease process in both AD and non-AD patients by increasing the amount of functioning ApoE.

Although, the role of ApoE4 has been best studied in Alzheimer's disease, we believe ApoE is crucial for the functional recovery and enhanced survival of neurons in non-AD neurodegenerative diseases. Hence, regulating ApoE levels may alter the rate of progression or influence the age of onset and/or death of a host of neurodegenerative diseases. Thus, pharmaceuticals that allow for the manipulation of ApoE levels will be useful reagents for the treatment of many neurodegenerative diseases.

We predict that drug responsiveness may be dependent upon the ApoE phenotype in Alzheimer's disease. Because of the role of ApoE in reinnervation and synaptic replacement in the brain, we postulate that the presence of the ApoE4 will not only affect drug responsiveness in Alzheimer's disease, but that it will also affect drug responsiveness in other neurodegenerative diseases of the CNS, particularly where apoE4 allele load has been shown to affect symptomology.

We believe that the observed reduction in brain ApoE levels reported in apoE4 carriers results in defective delivery of cholesterol and phospholipids into neurons. In this model, the LDL receptor family is playing a crucial role in mediating the internalization of the ApoE lipoprotein-complexes. The internalized lipids indeed constitute the building blocks for the formation of membrane, terminal and synapto-dendritic structures. We hypothesize that the impaired delivery of major membrane lipids in E4 carriers compromises synaptic integrity (as reported by Masliah et al., 1995), pre-synaptic terminal structures, (as indicated by the losses of ChAT activity in the hippocampus and cortex of apoE4/AD subjects) ultimately leading to impaired cognitive performance.

Drugs Suitable for Increasing ApoE Levels

Figure 6:
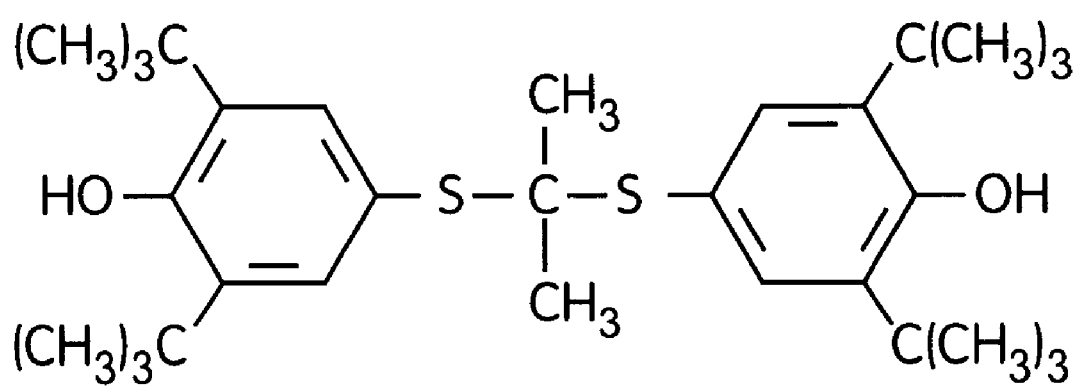
FIG. 6 is a drawing showing the molecular structure of probucol.

The methods provided herein make use of probucol (Lorelco™) prepared by and commercially available from Marion Merrell Dow Inc. Nonetheless, we predict that the following other drugs namely, tacrine (Cognex™, manufactured by Parke-Davis), heptylphysostigmine (manufactured by Merck Corp.), simvastatin (Zocor™, manufactured by Merck Corp.), lovastatin (Mevacor™, manufactured by Merck Corp.), pravastatin (Pravachol, manufactured by Bristol-Myers Squibb), thorvastatin (Parke-Davis), probucol analogs, vitamin E, donepezil (Aricept™), blood pressure inhibitors, antioxidants, anti-all inflammatories, and steroids are suitable for altering ApoE levels and eliciting similar beneficial effects for the treatment of the afflictions described herein. The molecular structure of probucol is provided in FIG. 6. The compounds described above are all commercially available and have established dosage protocols.

It will be appreciated that other compositions which raise ApoE levels may be identified using the assays provided herein.

We predict that the primary efficacy of these compounds and compositions rests with their ability to increase levels of ApoE. We have developed an efficient bioassay to screen for useful drugs capable of increasing ApoE levels. A cell culture system using an primary rat astrocyte cell line is exposed to varying concentrations of probucol or any other potential drug and ApoE levels are measured at the mRNA level or protein level. Other culture systems which may be used include human culture systems of primary cells derived from human tissue or immortalized cell lines of nerve tissue origin such as the human astrocyte cell line, AsCH-7 (Bobryshev et al., 1995). In addition, novel cell lines from patients with various apoE genotypes may be used, as well as cell lines from patients suffering or predisposed to suffer from any of the neurodegenerative diseases described herein. Adult spinal cord from post-mortem patients with any of the above diseases may be used as a source for deriving cell lines of nerve tissue origin. One method of immortalizing cells from these patients E a is to infect primary tissue with a replication-deficient retrovirus containing DNA sequences encoding the SV40 large T antigen (Whittemore et al., 1994). Another method is to derive immortal human-human hybrid cell lines that express phenotypic characteristics of primary oligodendrocytes or astrocytes by fusing a 6-thioguanine-resistant mutant of the human rhabdomyosarcoma RD cell line with adult human nerve tissue by a lectin-enhanced polyethylene glycol procedure (McLaurin et al., 1995). Other methods for immortalizing cells derived from primary human nerve tissue could include the use of chemical carcinogens or radiation. The use of animal models such as mice with mutations or gene disruptions of any genes known to contribute to any of the diseases described herein is also a source of nerve tissue to be used in a cell based assay for the screening of drugs capable of increasing ApoE levels. Immortalized lines obtained in this manner would possess the genetic lesion of the disease in question and provide a source for screening ApoE inducing pharmaceuticals uniquely suited for that particular neurodegenerative disease. Antibodies to ApoE allow for the design of a high throughput assay using an immunoassay detection method.

One particular application of this assay would be to evaluate the potency of probucol analogs for inducing ApoE expression. These analogs of probucol lack the anti-oxidant properties of probucol and would either lack the hydroxyl group/s (OH) or contain a modified hydroxyl group/s. In general, methods for producing probucol analogs include the condensation of 4-mercapto-2,6-disubstituted phenols with acetone. The synthetic yields for probucol are approximately 90% while the yields for other analogs are variable but normally greater than 40%. Such analogs provide an opportunity to dissociate the anti-oxidant properties of probucol from the ApoE inducing properties of probucol. If probucol analogs increase ApoE levels in the cellular screening assay, then this would demonstrate that ApoE induction is an antioxidant independent mechanism.

Further, we have observed that compounds such as heptylphysostigmine, tacrine, and various HMG CoA reductase inhibitors increase the levels of extracellular ApoE in the astrocyte screening assay. In contrast, the specific acetylcholinesterase inhibitor donepezil had no effect on secreted ApoE levels. These results indicate that a variety of known drugs can modulate the extracellular levels of ApoE in an antioxidant independent way and suggest that the antioxidant properties of probucol may not be critical to the mechanism responsible for increases in ApoE.

Administration of Probucol-Containing and Tacrine-Containing Compositions

Probucol-containing and tacrine-containing compounds, such as Lorelco™ and Cognex™ are commercially available from Marion Merrell Dow Co. and Parke-Davis, respectively. The clinical dosage form for oral administration of Lorelco™ is either a 250 mg or 500 mg tablet. Preferably, tablets are administered at a dosage of at least 500 mg twice daily by oral administration. Cognex is available in the form of a 10 mg or 40 mg capsule and can be titrated up to 160 mg per day by oral administration.

Other formulations for treatment or prevention of the conditions described herein, may take the form of a compound that alters ApoE levels and may be combined with a pharmaceutically-acceptable diluent, carrier, stabilizer, or excipient. Conventional pharmaceutical practice is employed to provide suitable formulations or compositions to administer such compositions to patients. Oral administration is preferred, but any other appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, or aerosol administration. Therapeutic formulations may be in the form of liquid solutions or suspensions (as, for example, for intravenous administration); for oral administration, formulations may be in the form of liquids, tablets or capsules; and for intranasal formulations, in the form of powders, nasal drops, or aerosols.

Methods well known in the art for making formulations are described, for example, in "Remington's Pharmaceutical Sciences," Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes.

If desired, slow release or extended release delivery systems may be utilized. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

In general, probucol or tacrine, or other compounds for use in the methods of the invention are administered at a dosage appropriate to the effect to be achieved and are typically administered in unit dosage form. As noted above, the preferred route of administration for most indications is oral.

An effective quantity of a probucol-containing, tacrine-containing, or the other compound of the invention is employed to treat the conditions described iherein. The exact dosage of the compound may be dependent, for example, upon the age and weight of the recipient, the route of administration, and the severity and nature of the symptoms to be treated. In general, the dosage selected should be sufficient to prevent, ameliorate, or treat the condition, or one or more symptoms thereof, without producing significant toxic or undesirable side effects.

The bioassays described in Example 9 can also be employed in determining dosage for known and unknown drugs such that a therapeutically effective amount necessary to increase ApoE levels in cells of nerve tissue origin could be determined.

In the case of probucol, there is no acute toxicity in mice or rats. A single case of an overdose in a human was resolved by induced vomiting and the patient had no lasting ill effects.

The following detailed examples are provided for the purpose of illustrating, and not limiting, the invention.

EXAMPLE 1

ApoE-/-Mice Exhibit Neuronal Deficits

Homozygous apoE-deficient (knockout) mice display a significant loss m of synapses and marked disruption of the dendritic cytoskeleton with normal aging. More importantly, these animals failed to show compensatory synaptogenesis following lesions of entorhinal cortex projections. The importance of ApoE in brain lipid transport is further underscored by the absence of other key plasma apolipoproteins such as apoA1 and apoB in brain tissues.

Figure 2:
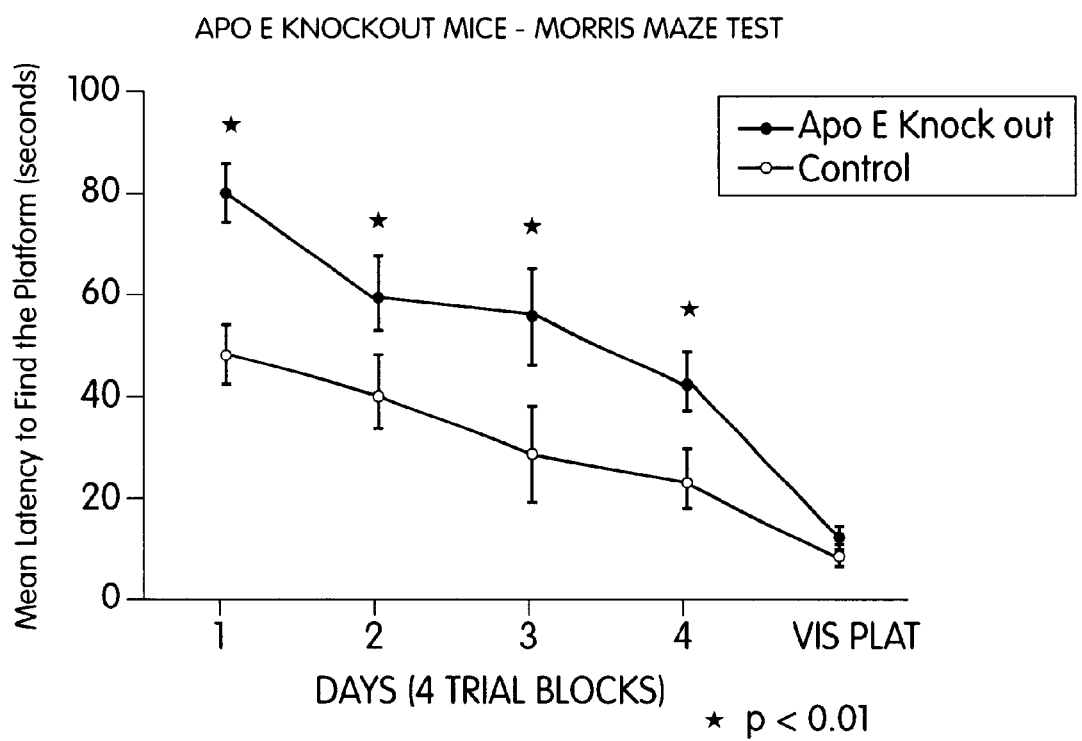
FIG. 2 is a graph depicting the difference in latency performance in a Morris swimmaze for a 3 month old control mouse versus a heterozygote apoE knockout mouse.

Analysis of spatial memory performance in the Morris swimmaze of ten apoE knockout mice and ten control mice cross-bred to homogeneity in a C57B1 genetic background revealed marked impairment of cognitive performance in 3, 5, and 6 month old animals. These genetically stabilized apoE knockout mice (~99% pure C57B1 background) are derived from the North Carolina apoE knockout mice colony. Briefly, mice (control and heterozygote apoE knockouts) were placed into a 1.6 m diameter pool filled (45 cm depth) with water made opaque by the addition of powdered skim milk. The animals must locate a platform submerged 2 cm below the surface of the water. Animals finding the platform within 120 sec were allowed to stay on the platform for 30 sec and then removed. Each mouse was given 4 trials per day for four days of testing. The primary dependent variables measured are the latency and distance to find the platform. FIG. 2 summarizes the latency results obtained in young (3 months old) homozygote apoE knockout mice versus control mice. Detailed analyses of swimming speed and pattern as well as visual deficits revealed no impairment in either motor or visual coordination in the knockout mice.

These results indicate synaptic integrity and plasticity, as well as spatial memory performances, are seriously compromised by the absence of ApoE in the brain. Interestingly, regeneration and plasticity are relatively intact in the injured PNS in apoE knockout mice where, in contrast to the CNS, apoB, apoj and apoA1 behave like back-up systems for the transport of lipids during neural tissue remodeling.

EXAMPLE 2

Apolipoprotein E4 and Alzheimer's Disease

Alzheimer's disease pathology is characterized by an early and extensive loss of entorhinal cortex neurons and a marked loss of neurons in the hippocampal CA1 area. However, in contrast to the entorhinal cortex lesioned rat brain, only a small number of AD patients (with undetermined apoE genotype) are capable of displaying synaptic plasticity in response to hippocampal deafferentation. It has also been shown that there are significant decreases in presynaptic terminal density (−45%) in the neocortex and in layer V of the frontal (−27%) and temporal cortices (−36%). We predict that these pathologies observed in AD are linked to abnormal ApoE metabolism.

Indeed, the link between ApoE metabolism and AD is supported by genetic findings that demonstrate overlap with ApoE neurobiology and AD. The frequency of the apoE4 allele was shown to be markedly increased in sporadic as well as in late onset familial Alzheimer's disease. A gene dosage effect was observed in both familial and sporadic cases: i.e., as age of onset increases, apo E4 allele copy number decreases.

The apoE4 allele prevalence analyses in both living (probable) AD patients and autopsied (confirmed) AD subjects from Eastern Canada indicate that as many as 80% of all our AD subjects, aged 65 to 75, are carriers of at least one copy of the apoE4 allele. The apoE4 allele dosage also is observed to modulate the age of onset in AD families with the amyloid precursor protein (APP) mutation on chromosome 21 and in AD families with mutations in the presenilin 2 gene on chromosome 1. Families with chromosome 14-linked AD are apparently not affected by the apoE4 allele.

The apoE4 allele copy number was also shown to have an impact on: 1) the risk of developing AD; 2) the accumulation of mature senile (amyloid) plaques and tangles in the cortex and hippocampus; 3) cholinergic cell density in the basal forebrain; 4)choline acetyltransferase activity and nicotinic receptor binding sites in the hippocampus and temporal cortex, and; 5) neurofibrillary tangles density.

These results indicate the existence of a very close relationship between the apoE4 allele dosage and the neuropathology of AD. For example, AD subjects carrying at least one copy of the apoE4 allele exhibit a marked reduction of synapse density when compared to apoE3/3 AD subjects or to age-matched control individuals.

EXAMPLE 3

ApoE4 and Cholinergic Dysfinction in AD

Brain membrane phospholipids, especially phosphatidylcholine (PC) and phosphatidylethanolamine (PE), have been shown to be involved in the availability of choline, a rate-limiting precursor of acetylcholine (ACh). The release from PC of free choline precursor for ACb synthesis is accomplished in a one step process through a phospholipase-D type enzyme in cholinergic neurons. Brain levels of choline are decreased by up to 40–50% in frontal and parietal cortices of AD patients whereas cholesterol, which is required for the proper functioning of the nicotinic receptor sub-type, is markedly reduced in AD versus control subjects.

As losses of cholinergic neurons and/or choline acetyltransferase (ChAT) activity are well known neurochemical hallmarks of AD, the relationship between the apoE4 genotype and cholinergic deficits is highly relevant to investigate in genetically distinct individuals. Thus, we quantified cholinergic neuron density in the nucleus basalis of Meynert and in the diagonal band of Broca in post-mortem AD subjects with and without the apoE4 allele. We also examined the impact of cholinergic cell reduction on cholinergic markers in the brain areas that receive cholinergic input from these brain areas, namely, the hippocampus and the cortex.

The cholinergic markers examined were the choline acetyltransferase activity (ChAT: essentially pre-synaptic) and nicotinic receptor (NR: largely pre-synaptic) in control and AD subjects carrying 0 (E3/3), 1 (E4/3) or 2 (E4/4) copies of the apoE4 allele. FIG. 3 summarizes our findings. Although reductions in cholinergic neuron density were found in apoE4 and non-apoE4 AD subjects at the level of the nucleus basalis of Meynert (middle graphs) and the diagonal band of Broca, only AD subjects carrying 1 or 2 copies of E4 showed significant loss of pre-synaptic ChAT and NR in the hippocampus and temporal cortex. In other words, apoE3/3 AD subjects, despite a 60 to 70% cell loss in the basalis, manage to maintain cortical and hippocampal ChAT activities and NR densities within normal range.

These results are consistent with the theory that the apoE genotype may directly influence the synaptic plasticity of the cholinergic system in response to neuronal cell loss. In this model, ApoE4 compromises lipid homeostasis and consequently impairs membrane remodeling. These results demonstrate that cholinergic reinnervation and synaptic plasticity are markedly compromised in several brain areas in Alzheimer's disease subjects carrying 1 or 2 copies of apoE4. Furthermore, when the extent of the regeneration potential of E4 and non-E4 carriers was quantified, a massive reduction in the overall regenerative capacity of apoE4 subjects in at least six different brain regions was observed.

EXAMPLE 4 apoE4 Carriers and ApoE Concentrations in the Brain

We have observed that there is a relationship between synaptic integrity, reinnervation in the brain, and ApoE levels and this is supported by two otherwise disparate observations: a) the complete absence of ApoE compromises synaptic density, reinnervation and plasticity and, b) successful synaptic remodeling in the intact animal is associated with the over expression of ApoE in the deafferented zone.

In the AD brain, apoE MRNA was shown to be present but not increase in response to cell loss and deafferentation. FIG. 4 illustrates levels of ApoE measured in the brain of AD subjects with different genotypes as well as in control subjects with apoE3/2 and apoE3/3 genotypes. Of the ~90 neuropathological elderly control subjects that we have examined so far (using standard criteria), none of those fitting the "CONTROL" criteria were found to carry the E4 allele. A significant reduction in ApoE concentration in tissue was measured in apoE4 carriers versus non-E4 subjects.

We have discovered that the risk of developing AD, the accumulation of senile plaques and tangles in the AD brain, and the loss of cholinergic function in AD follow the exact same genotype gradient as the concentration of ApoE measured in the brain of AD subjects: i.e., increasing marked deterioration is observed in genotypes E2/2, E3/3, and, E4/4, the latter genotype representing the worse case scenario. We believe that the most important observation among these is the fact that the Alzheimer pathology is much more severe (cell loss, deafferentation, and increased GFAP expression) in apoE4 carriers having AD than it is in the non-apoE4 AD subjects. Yet, ApoE levels, which should be increased in response to damage and cell loss, are in fact decreased in those same ApoE4 individuals. We believe this decrease points to an underlying mechanism of the pathology of neurodegenerative disease.

EXAMPLE 5

Pathophysiological Consequences of Low ApoE Levels

To address the pathophysiological consequences of having low ApoE levels in life long apoE4/AD carriers we examined apoE/apoB (LDL) receptor expression (which correlates with cholesterol internalization) and HMG-CoA reductase expression (cholesterol synthesis) in the hippocampus AD and control subjects with different apoE genotypes. This comparison allows us to assess the consequences of the poor delivery of lipids in apoE4 carriers.

Table 1 summarizes the mRNA prevalence measured for the LDL receptor, HMG-CoA reductase and glial fibrillary acidic protein (GFAP) in post-mortem brains of control and AD subjects with known apoE genotypes. Beta-tubulin was used as a control transcript to adjust for RNA loading in the gels. GFAP mRNA prevalence, a well known marker of local tissue damage is markedly increased in apoE4 carriers when compared to apoE3/3 AD subjects. This supports the theory that more severe damage occurs in the brain of apoE4 carriers. The LDL receptor and HMG-CoA reductase mRNA prevalence were found to be increased in AD subjects carrying the apoE4 allele when compared to non-E4 carriers.

TABLE 1 mRNA Levels of GFAP, LDL, and HMG-CoA in Post Mortem Brain Samples of Patients with AD
mRNA Prevalence in the Hippocampus of AD Patients

| Genes | ApoE3/3 | ApoE4/3 | ApoE4/4 |
|---|---|---|---|
| | % OF CONTROLS | | |
| GFAP | 110 | 365* | 345* |
| LDL | 86.5 | 173* | 170* |
| HMG-CoA | 87 | 191* | 152 |
| | N = 6 | N = 7 | N = 3 |

*: p<0.05

The reduction of total brain ApoE protein in apoE4 carriers is sufficient to shift cholesterol metabolism from its nornal steady state concentration to a depleted state. This forces cells to attempt to compensate by upregulating both synthesis and internalization. Thus we believe that ApoE depletion observed in the brain of apoE4 carriers may significantly compromise lipid delivery in the CNS in a manner which cannot be compensated for by the usual compensatory mechanisms. Ultimately, the damage to nerve tissue is thus exacerbated. These results provide us with an entirely novel explanation for the reported reduction of cholesterol in the brain of AD subjects with unknown genotype.

EXAMPLE 6

Alteration of Apo E Levels as the Basis of a New Therapeutical Approach for AD

It has been recently demonstrated that chronic (1 month) intraventricular infusion of purified human ApoE3 and ApoE4 in apoe knockout mice effectively restored microtubulin-associated protein 2 and synaptophysin-like immunoreactivities in the cortex of homozygote knockout animals. This result indicates that both ApoE4 and ApoE3 are effective in restoring dendritic integrity in the ApoE knock-out mice. More importantly, the effect of intracerebral infusion of ApoE3 and ApoE4 on cognitive performance and spatial memory function in the apoE knockout mice was examined and it was observed to be improved. This is consistent with the fact that ApoE4 is as good as ApoE3 at binding to the LDL receptor and carrying lipids in the serum. However, in contrast to ApoE3, ApoE4 concentration is much lower in the serum and in the brain of apoE4 carriers.

From these observations we concluded that manipulation of ApoE concentrations in the brain of mammals will effectively restore synaptic plasticity and reinnervation in the brain. The results summarized above indicate that there is nothing particularly toxic or detrimental with the ApoE4 isoform, but rather that the metabolism of ApoE4 leads to lower concentration of ApoE in the brain of E4 carriers, as compared to non-E4 carriers.

EXAMPLE 7

Proof of Principle of this Therapeutical Approach for Alzheimer's Disease Using Tacrine Using astrocyte cell cultures, we recently screened several Alzheimer- and cardiovascular-related drugs which are known to affect lipid metabolism in vivo for their effect on ApoE levels. One known antidementia drug, called tacrine or "Cognex™" (manufactured by Parke-Davis), was found to act as an inducer of ApoE synthesis and ApoE secretion in astrocytes in culture. Tacrine is one of two FDA approved drugs to treat Alzheimer's disease in the U.S. It improves memory and learning functions in Alzheimer's disease by inhibiting acetylcholine degradation (acetylcholinesterase inhibitor). We conclude from our results that tacrine achieves its beneficial effect by this effect on ApoE synthesis.

Importantly, tacrine has been shown to delay institutionalization by more than 1.5 years in Alzheimer's patients treated for a very long periods of time. These results are interpreted as evidence for a beneficial effect of tacrine on the rate of deterioration of Alzheimer's disease that occurs more or less independently from cholinergic effect on memory performance. We propose that the effects of tacrine on lipoprotein homeostasis indicates that tacrine may affect lipid homeostasis in the brain by interacting with esterases that control HDL homeostasis and delivery to brain cells. This mode of action of tacrine in the CNS may contribute to the observed long-term beneficial effect of tacrine on slowing down disease progression in AD.

Figure 5:
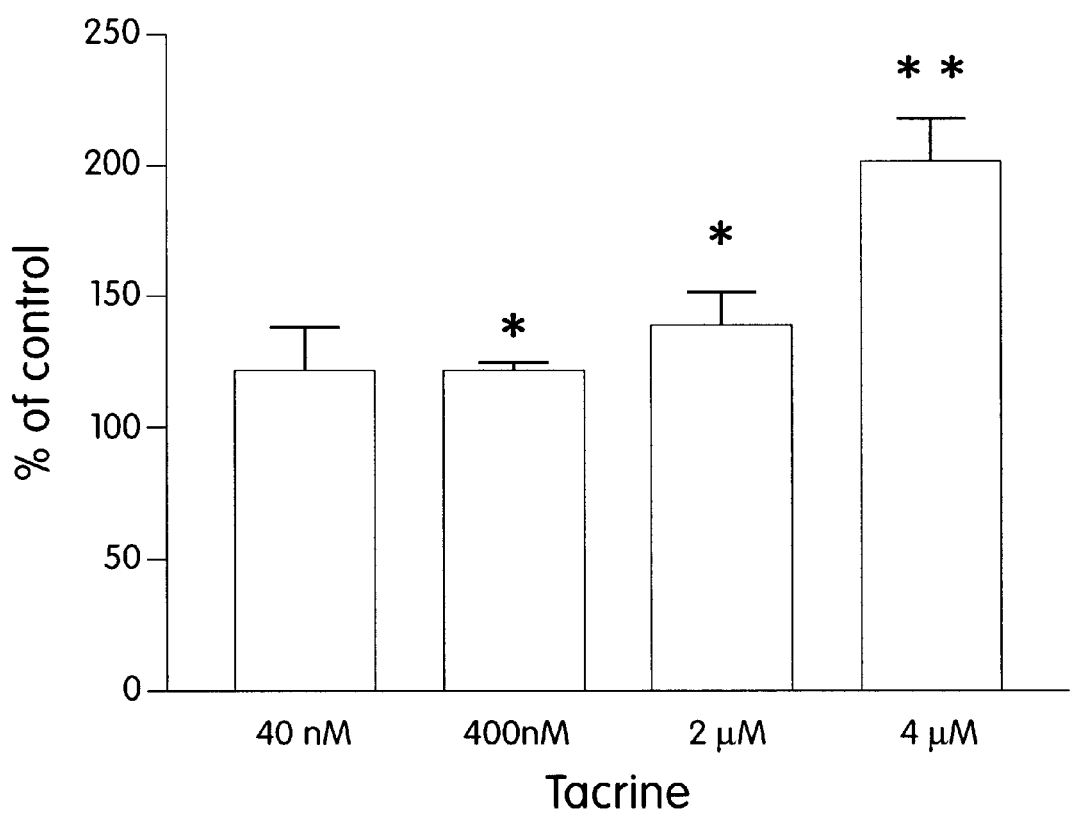
FIG. 5 is a histogram depicting the effect of various concentrations of tacrine on secreted ApoE levels in rat type-I astrocytes in culture.

To verify this working hypothesis, we have examined the effect of vanous concentration of tacrine on ApoE synthesis and secretion in brain cells in culture. FIG. 5 illustrates the effect of tacrine on ApoE secretion in rat type 1 astrocyte cultures exposed (for 8 hours) to physiological and pharmacological concentrations of the drug. Tacrine increases ApoE secretion in astrocytes at concentrations typically found in the CSF of AD patients treated for several weeks with tacrine (2 uM). We recently examined cerebrospinal fluid concentration of ApoE in living AD subjects treated with tacrine for several months and found higher levels of ApoE (N=4: nearly significant despite small sample size) in the drug treated patients compared to untreated AD subjects (Table 2). Experimental methods used to monitor ApoE levels are described in Bertrand et al., Mol. Brain Res. 33:174–178 (1995).

TABLE 2

ApoE Levels in the CSF of Patients with AD Treated and Untreated with Tacrine

| | ApoE Concentration (mg/dL) In the Cerebrospinal Fluid (CSF) | | | |
|---|---|---|---|---|
| | Controls (Age Matched) | Alzheimer | Alzheimer + Tacrine | p values A vs A + T |
| Mean | 0.42 | 0.36* | 0.41 | *0.09 |
| S.E.M. | 0.02 | 0.02 | 0.06 | |
| N = | 16 | 30 | 4 | |

In conclusion, while it is known that tacrine improves memory in AD patients and delays institutionalization by 1.5 years we have made the novel discovery that the mechanism by which this drug works is to cause ApoE synthesis and secretion in vitro at physiological concentrations in brain cells and finally, to cause a raise in cerebrospinal fluid concentration of ApoE in living patients and to slow down disease progression to a point where it delays institutionalization. These observations suggest that the effect of tacrine on Alzheimer's disease progression is caused by its action on ApoE synthesis and secretion. This observation is entirely consistent with the results obtained in the memory impaired apoE knockout mice exposed to physiological or intracerebral levels of purified ApoE.

On that basis we claim that agents with properties like tacrine, such as probucol, heptylphysostigmine, simvastatin, lovastatin, pravastatin, thorvastatin, probucol analogs, vitamin E, Aricept, blood pressure inhibitors, antioxidants, anti-inflammatories, and steroids may be capable of inducing ApoE synthesis and secretion in brain cells, and therefore represent very potent promoters of synaptic plasticity and reinnervation in the normal brain. We forecast they should slow down Alzheimer's disease progression and delay the arrival of the Alzheimer's disease in those who are at risk but not yet symptomatic. These agents should also have therapeutic effects in other neurodegenerative disease where synaptic plasticity and reinnervation are at least in part compromised by the disease state.

EXAMPLE 8

Probucol for the Treatment of Neurodegenerative Disease

Several drugs were developed over the past decade to alter blood lipid content in individuals who are at risk of developing cardiovascular diseases. One of these drugs, probucol (see FIG. 6), was developed in the 1960s by Dow Chemical Co. as a cholesterol lowering agent. Probucol is a very safe compound that also exhibits potent antioxidant properties. It was shown recently that subjects carrying the apoE4 allele were more responsive to the cholesterol lowering activity of probucol than subjects not carrying this allele. Circulating ApoE levels were shown to be increased in probucol-treated hypercholesterolemic patients. Probucol was shown to be totally uneffective in subjects with a very high physiological concentration of ApoE that exhibit the apoE2/2 genotype. Probucol is also known to lower total plasma apoB, apoA-1, apoA-II, apoC-II and apoC-III, all of which have little or no role to play in brain lipid homeostasis. The effect of peripheral administration of probucol on CNS apolipoproteins is unknown in human.

FIG. 7 illustrates results obtained from rat primary type 1 astrocyte cultures exposed to probucol at concentrations of 1 nM, 100 nM, and 10 uM for 24 and 48 hours. Apo E concentration was assessed in the cell culture medium by immunoblot analysis using methods previously described (Poirier et al., *Neuroscience*, 55:81–90 (1993)). In the absence of probucol (EtOH control) very little ApoE is detected in the media (i.e., the extracellular compartment). In contrast, concentrations of probucol as low as lnM dramatically increased the extracellular amount of ApoE at 24 hours post dosing. Further increases in ApoE were observed with increasing concentrations of probucol. We also observed that the amount of ApoE detected in the media at 48 hours was less than the amount of ApoE in the media after only 24 hours of incubation. This time-dependent response in ApoE levels may reflect the continued division and growth of cells.

In summary, in a manner similar to tacrine, pharmacological concentrations of probucol were shown to cause marked synthesis and secretion of ApoE in the astrocyte cultures media. These in vitro results indicate that astrocytes, the cells responsible for the synthesis of ApoE in the brain, secrete large amounts of ApoE when exposed to probucol in vitro.

EXAMPLE 9

In Vivo Model for Determining the Effect of Probucol on ApoE levels

Figure 8:
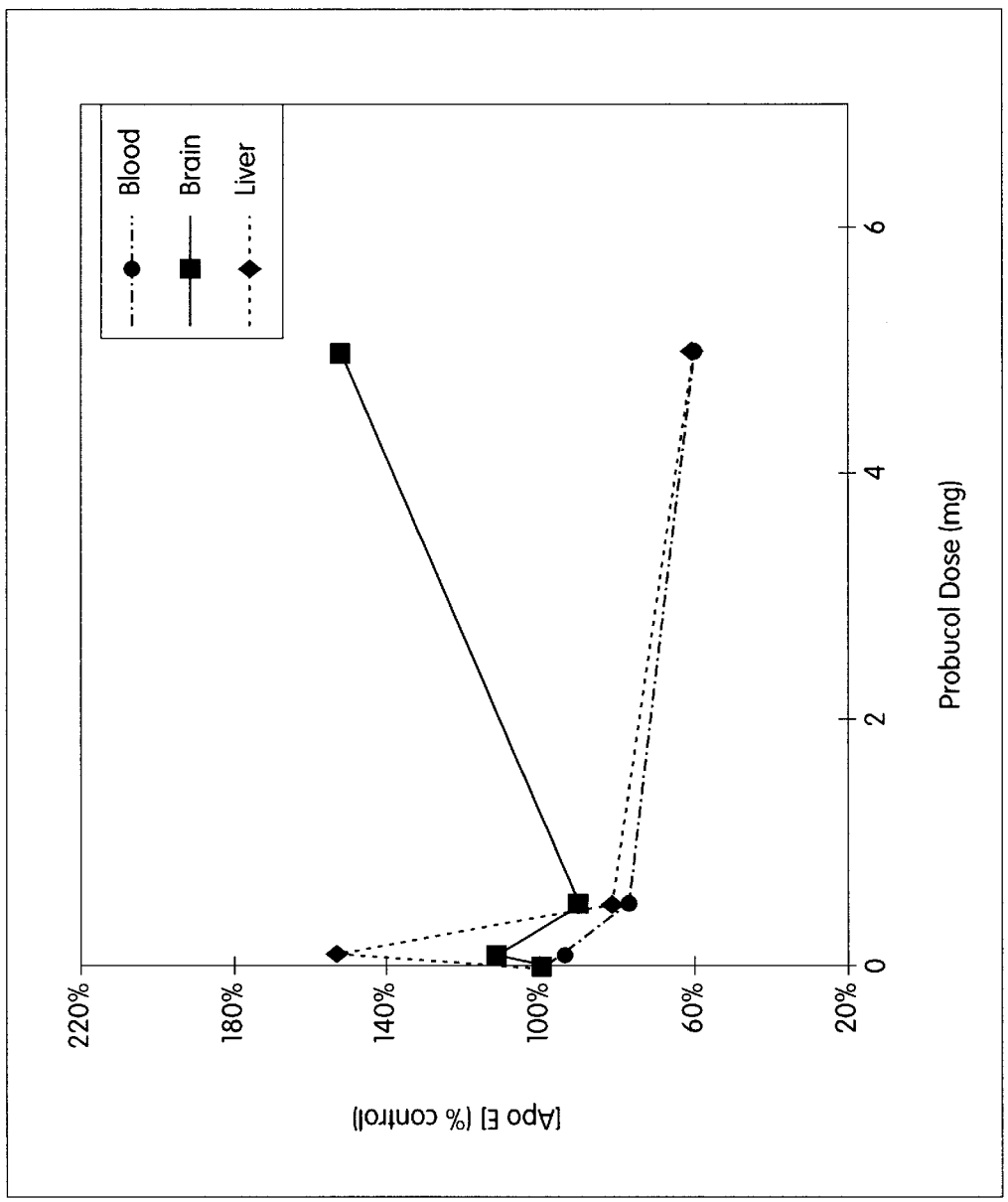
FIG. 8 is a graph that shows the dose response of ApoE levels in different murine tissues following 10 days of treatment with probucol.

To extend the foregoing in vitro studies, the following animal study was conducted. Mice were dosed (i.p.) with probucol daily for ten days at doses ranging from 0.1 to 5 mg. At the end often days, the animals were sacrificed and the brain tissue collected, rapidly dissected, and the hippocampi were isolated. The livers, tissue, and blood were also collected. Tissue homogenates from all ten animals were pooled and the ApoE levels in the different tissues were determined by immunoblot. The intensity of the bands on the immunoblot were quantitated by scanning densitometiy and these results are summarized in Table 3 and graphically represented in FIG. 8.

In animals treated with probucol (highest dose), ApoE levels increased dramatically in brain tissue but not in other tissues tested (i.e., blood, liver). In the blood, the levels of ApoE decreased in the presence of probucol and continued to decrease with increasing doses. The levels of ApoE in the liver initially increased but then decreased at the higher doses of probucol. At the highest administered dose (5 mg), the levels of ApoE in the blood and liver were reduced to 60% of the control values for these tissues. In contrast, the levels of ApoE in the brain increased to approximately 150% of the control value at the highest dose evaluated. We believe the different responses may reflect 1) differences in the distribution of probucol in the different tissue compartments and/or 2) tissue specific effects of probucol on the expression and secretion of ApoE.

TABLE 3

In Vivo Effect of Probucol on ApoE Levels in Different Murine Tissues*

| Tissue Sample | Probucol Dose (mg) | G/Dens-DD | G/DxA (% Total) | G/Dens (% Peak) |
|---|---|---|---|---|
| Blood | control | 0.2941 | 20.274 | 74.900 |
| | 0.1 | 0.2783 | 19.187 | 70.886 |
| | 0.5 | 0.2262 | 14.885 | 57.610 |
| | 5.0 | 0.1800 | 11.846 | 45.847 |
| rApoE (10 ng) | | 0.0024 | 0.149 | 0.604 |
| Hippocampus | control | 0.0653 | 4.092 | 16.629 |
| | 0.1 | 0.0729 | 4.570 | 18.571 |
| | 0.5 | 0.0587 | 3.497 | 14.958 |
| | 5.0 | 0.1000 | 5.954 | 25.469 |
| rApoE (20 ng) | | 0.0292 | 1.831 | 7.441 |
| Liver | control | 0.0540 | 3.216 | 13.759 |
| | 0.1 | 0.0840 | 5.263 | 21.386 |
| | 0.5 | 0.0444 | 2.506 | 11.315 |
| | 5.0 | 0.0325 | 1.933 | 8.268 |

*= measured by scanning densitometry of immunoblots

EXAMPLE 10

Human Clinical Trial to Determine the Effect of Probucol Administration on Cerebrospinal Fluid (CSF) ApoE Levels and on the Clinical Manifestations of AD Patients with Different apoE Genotypes We have conducted a clinical trial to investigate the potential utility of probucol as a therapeutic agent for altering disease progression in Alzheimer's disease. Our initial hypothesis was that AD patients who are apoE4 carriers are characterized by a defective system of repair due to lower ApoE brain levels. Accordingly, in these patients, it should be possible to either stop or slow down the disease process by increasing the amount of normally functioning ApoE.

To test this hypothesis, patients with AD with apoE3/3 and 4/3 phenotypes were treated with probucol for a period of six months and the effect of that treatment on the cerebrospinal fluid (CSF) levels of ApoE and on clinical scales of cognitive functioning were documented.

Experimental Design and Methods

A total of 8 patients with AD participated in this study. After determination of the ApoE phenotype at a baseline evaluation, all patients received probucol.

Inclusion criteria were the following: 1) patients were between 50 and 80 years of age; 2) women were postmenopausal or surgically sterile; 3) patients had a clinical diagnosis of probable Alzheimer's disease; 4) subjects were fluent in French or English (able to write, read, speak, and understand); 5) the availability of an informant was required; 6) patients had a severity index between 10 to 26 on the Mini-Mental State Examination (MMSE); 7) patients who had taken an investigational drug less than four months before the baseline were excluded; and, 8) the following medications were disallowed (should not be taken four months before baseline): cimetidine, lipophilic beta-blocker (propranolol), clonidine, anticholinergics, and antidepressant with anticholinergic activity (tricyclics), neuroleptics, putative cognitive enhancers and central nervous system stimulants, or benzodiazepines with a long half life.

The demographic data of the patients in this study are summarized in Table 4. Patients with a clinical diagnosis of probable Alzheimer's disease were Ad recruited through the memory clinic at the Douglas Hospital (Montreal, Canada). The mean age of onset of the disease was 65, younger than observed in most large clinical drug trials. These patients were all in the early stages of the disease as measured by an average MMSE score of 17.3, one year after their initial diagnosis.

TABLE 4

Patient Demographic Data for Clinical Trial

Patient Demographic Table

| Patient | age (study) | Sex | age (diagnosed) | education | MMSE |
|---|---|---|---|---|---|
| PP-101 | 58 | 2 | 57 | 11 | 15 |
| PP-102 | 66 | 1 | 64 | 10 | 19 |
| PP-103 | 60 | 1 | 59 | 20 | 19 |
| PP-104 | 78 | 1 | 77 | 7 | 20 |
| PP-105 | 74 | 2 | 73 | 8 | 20 |
| PP-106 | 62 | 1 | 62 | 12 | 20 |
| PP-107 | 80 | 2 | 80 | 12 | 14 |
| PP-108 | 61 | 1 | 61 | 7 | 16 |
| PP-109 | 56 | 1 | 52 | 9 | 13 |
| Average | 66.1 | | 65 | 10.7 | 17.3 |

Primary Efficacy Parameters

Biological Marker:

A lumbar puncture was performed at baseline and one month after treatment. The relative concentrations of ApoE levels in the CSF were determined by immunoblot as described by Poirer, J. et al., *Neuroscience* 55:81–90 (1993).

Neuropsychological Assessment:

The Alzheimer's Disease Assessment Scale, Cognitive Part (ADAS-Cog) (see Rosen et al., *Am. J Psychiatr.*, 141:1356–1364 (1984)) was used as an objective neuropsychological measure. It consists of a battery of neuropsychological tests for different cognitive functions. The battery comes to a single score with a maximum of 70 points and is administered in about 45 minutes to patients. A 117 point extended scale version of this test was also used (see Table 5).

Secondary Efficacy Parameters

Biological Markers:

Additional biochemical markers included phenotyping of the patients ApoE and determining relative concentrations of tau protein, $\beta$-amyloid protein (1–42 and 1–40); and relative extent of lipid peroxidation.

Neuropsychological Assessment:

The Clinical Impression of Change (CIBIC-Plus) and the Global Deterioration Scale (GDS) were recorded at 3 and 6 months. The Clinical Impression of Change (CIBIC-Plus) consists of the holistic impression by the clinician of whether the patient has shown any change since baseline as rated on a seven point sale (marked, moderate, mild improvement, no change, or marked, moderate, mild decline). The Global Deterioration Scale rates clinically identifiable stages of dementia.

Other tests that are useful for evaluating cognitive function in AD are the Disability Assessment in Dementia (DAD) questionnaire (Gauthier L et al., Abstract Book of the Sixth Congress of the International Psychogeriatric Assoc., 1993), the Cornell depression scale (Alexopoulos et al. 1988)) and the Behave-AD test (Reisberg et al. 1987).

TABLE 5

Comparison of the Standard ADAS-Cog (70 point scoring method) and the Extended ADAS-Cog (117 point scoring method).

| Scale Item | 70 point scale | 117 point scale |
|---|---|---|
| word-recall task | mean number of words not recalled in 3 trials | |
| naming of objects and fingers | 0 = 0–2 items named incorrectly<br>1 = 3–5<br>2 = 6–8<br>3 = 9–11<br>4 = 12–14<br>5 = 15–17 | |
| commands | points equal the number of incorrect commands (max = 5) | points equal the number of correct commands (max = 5) |
| constructional praxis | points equal the number of incorrect drawings (max = 5) | points for every correct drawings (max = 5) |
| ideational praxis | points equal the number of components failed (max = 5) | points for each successful components (max = 5) |
| orientation | points equal the number of incorrect items (max = 8) | points for each correct item (max = 8) |
| word-recognition task | points equal the number of incorrectly recognized words (max = 12) | points for each correct identification (max = 48) |
| spoken ability | max 5 | not included |
| comprehension of spoken language | max 5 | not included |
| word finding difficulty in spontaneous speech | max 5 | not included |
| remembering test instructions | max 5 | not included |

Overview of Clinical Trial

Eight of the nine patients recruited for the study completed the six month course of treatment. Non-compliance by one of the patients (patient PP-107) resulted in removal of the patient from the study after the three-month visit.

Adverse effects related to the administration of probucol are usually relatively minor (e.g., diarrhea, flatulence, abdominal pain, and nausea). Other occasional adverse effects include asymptomatic prolongation of the Q-T interval, eosinophilia, paresthesia, and angioneurotic edema (Buckley et al., *Drugs*, 37:761–800 (1989)). No serious adverse events were reported. At the 3 month visit, the electrocardiograms for two of the patients in the study group showed an -asymptomatic prolongation of the QT interval. The electrocardiograms normalized after reducing the probucol dose from 1000 mg to 500 mg per day for the remaining three months of the study.

All nine patients underwent lumbar puncture scheduled at the first visit and after the first month. The CSF of 8 patients (1–6, 8, and 9) were analyzed for concentrations of ApoE and other biochemical markers. The lumbar punctures were well tolerated with no reported side effects.

We observed in eight (8) patients receiving probucol at 1000 mg/day, the concentration of ApoE in the cerebral spinal fluid (CSF) increased by an average of 125% (% of baseline) following one month of treatment. Neuropsychological assessment of these patients (over the 6 month course of probucol treatment) revealed a trend that suggested that patients with the greatest increase in CSF ApoE protein are more likely to show an improvement in cognitive functions (as evaluated on the ADAS-cog scale). These results establish the first etiologic treatment of AD based on ApoE metabolism and support the theory linking apoE4 and AD.

Effect of Probucol on the Concentration of Apolipoprotein E in the CSF

The cerebral spinal fluid (CSF) of the above subjects was analyzed for the concentration of ApoE protein by immunoblot using an internal standard. The results of this analysis are summarized in Table 6. The samples for the first six patients were analyzed independently of the last two patients, thus the scales for patients 1–6 are different from the scales for patients 8 and 9.

TABLE 6

Summary of ApoE Levels in Cerebral Spinal Fluid

| Patient | ApoE Baseline (ROD) | ApoE 1 month (ROD) | Change in ApoE (% baseline) | ApoE Genotype |
|---|---|---|---|---|
| PP-101 | 4.51 | 8.03 | 178% | 3/3 |
| PP-102 | 10.87 | 14.81 | 136% | 3/3 |
| PP-103 | 7.71 | 10.27 | 133% | 3/3 |
| PP-104 | 2.20 | 2.59 | 118% | 4/3 |
| PP-105 | 8.05 | 7.14 | 89% | 3/3 |
| PP-106 | 10.59 | 9.17 | 87% | 4/3 |
| PP-107 | | | | |
| PP-108 | 0.0713 | 0.1086 | 152% | 4/3 |
| PP-109 | 0.0819 | 0.0861 | 105% | 4/3 |
| | | Average Change | 125% | |

For the 8 patients receiving 1000 mg/day of probucol, the concentration of ApoE in the CSF increased by an average of 125% following one month of treatment. These results are consistent with our in vitro (Example 8) and in vivo animal results (Example 9). Two different genotypes (phenotypes), the E3/E3 and E4/E3, were represented in this group of patients. On average, the E3/E3 group appeared to respond better than the E4/E3 group, however the small study group limits any interpretation of genotype influence on ApoE induction.

Neuropsychological Assessments

In order to determine if probucol-induced increases in ApoE levels influenced patient outcome we conducted ADAS-Cog tests (70 point, and extended 117 point) to measure any changes in the cognitive functioning in patients with Alzheimer's disease. The range of parameters measured in each of the ADAS-Cog tests is summarized in Table 5. These tests are used as the standard instrument for demonstrating cognitive efficacy in Alzheimer's Disease drug trials, particularly in North America. The ADAS includes both cognitive (ADAS-Cog) and non-cognitive (ADAS-Noncog) subscales and the tests components of memory, language, and behavior. The standard ADAS-Cog test (70 pt.) is scored by errors, and a higher score indicates poorer performance.

Cognitive Function in AD Patients after Treatment with Probucol

Figure 9:
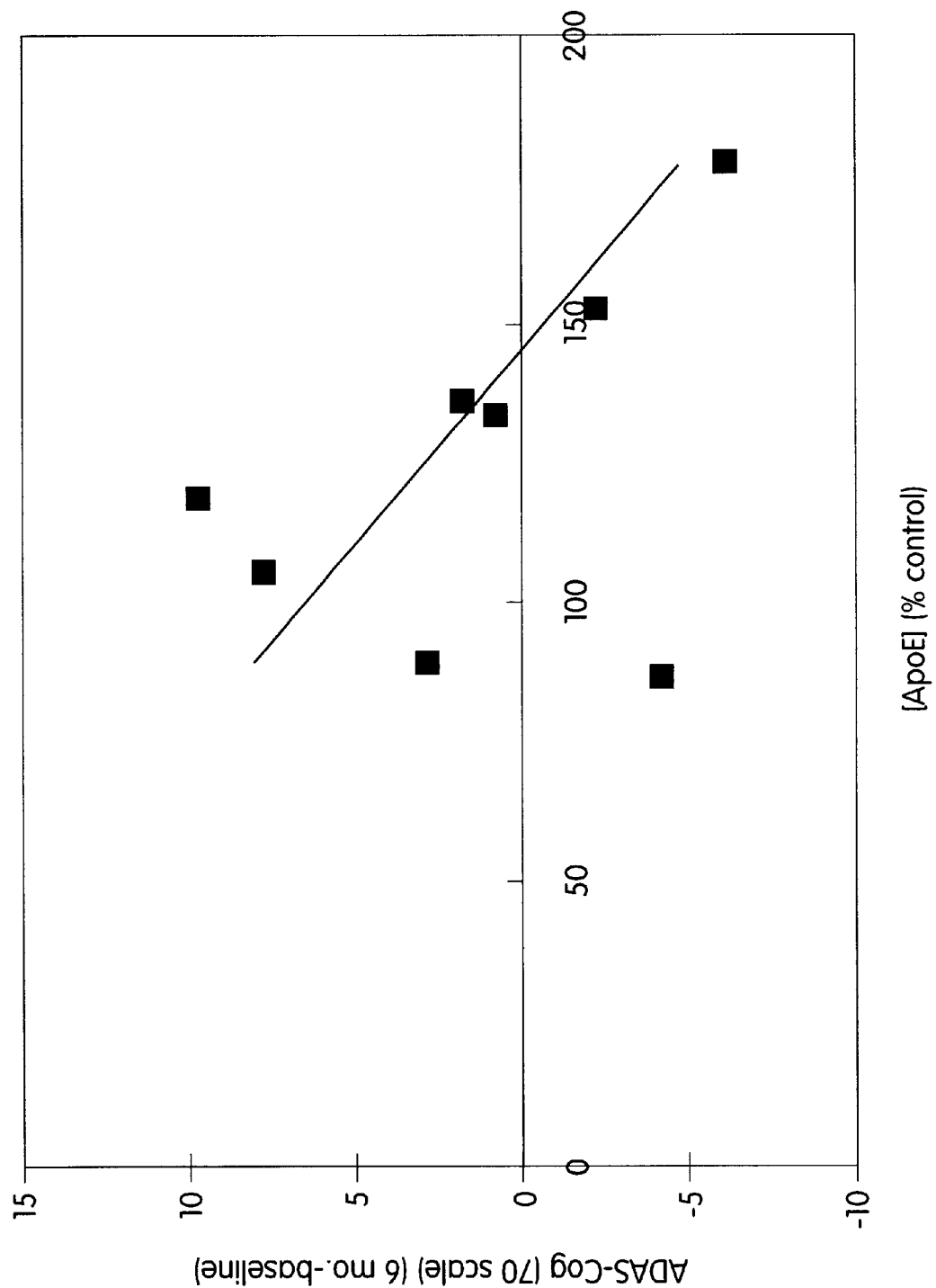
FIG. 9 is a graph representing the change in the ADAS-Cog Scores (70 pt. Scale) at six months as a function of change in ApoE levels in the CSF measured at one month.

We assessed the cognitive function of all subjects who completed 6 months of probucol treatment using the ADAS-Cog test (70 pt. scale). As shown in Table 7 and graphically in FIG. 9, a general trend in the data suggests that patients with the greatest increases in the apparent levels of ApoE protein in the CSF (measured at one month), are more likely to be stabilized or improved as judged by the changes in the ADAS-Cog scores over the 6 month course of treatment. We further assessed the cognitive finctioning of these patients with the extended scale ADAS-Cog test.

TABLE 7

ADAS-Cog (70 point scale) Scores for Patients that Completed Six Month Treatment with Probucol

| Patient | ADAS-Cog (70 point scale) | | |
|---|---|---|---|
| | Baseline | 3 months | 6 months |
| PP-101 | 31 | 29 | 25 |
| PP-102 | 34 | 34 | 36 |
| PP-103 | 24 | 28 | 23 |
| PP-104 | 30 | 37 | 40 |
| PP-105 | 41 | 41 | 44 |
| PP-106 | 20 | 22 | 16 |
| PP-107 | | withdrawn | |
| PP-108 | 19 | 18 | 17 |
| PP-109 | 32 | 27 | 40 |
| Average | 28.9 | 29.5 | 30.13 |

The extended 117 pt. ADAS-Cog test represents an alternative scoring approach that places more emphasis on the verbal memory demonstrated by the patient. The scoring method for this modified ADAS-Cog test ranges from 0 (the lowest score) to 117 (the best possible score).

As summarized in Table 8, five of the patients appeared to stabilize or improve over the course of the six month treatment. In particular, three of these patients showed significant increases (7-9 points). The remaining three patients decreased relative to baseline scores.

TABLE 8

Patient Cognitive Performance (as measured by ADAS-Cog (extended 117 point scale) during the Six Month Course of Treatment with Probucol

| Patient | ADAS-Cog (117 point scale) | | | |
|---|---|---|---|---|
| | Baseline | 3 months | 6 months | Genotype |
| PP-101 | 64 | 63 | 72 | E3/E3 |
| PP-102 | 64 | 63 | 65 | E3/E3 |
| PP-103 | 72 | 73 | 74 | E3/E3 |

TABLE 8-continued

Patient Cognitive Performance (as measured by ADAS-Cog (extended 117 point scale) during the Six Month Course of Treatment with Probucol

| Patient | ADAS-Cog (117 point scale) | | | |
|---|---|---|---|---|
| | Baseline | 3 months | 6 months | Genotype |
| PP-104 | 56 | 51 | 49 | E4/E3 |
| PP-105 | 73 | 73 | 82 | E3/E3 |
| PP-106 | 66 | 63 | 63 | E4/E3 |
| PP-107 | | withdrawn | | |
| PP-108 | 75 | 83 | 82 | E4/E3 |
| PP-109 | 64 | 56 | 58 | E4/E3 |
| Average | 66.8 | 65.6 | 68.1 | |

Figure 10:
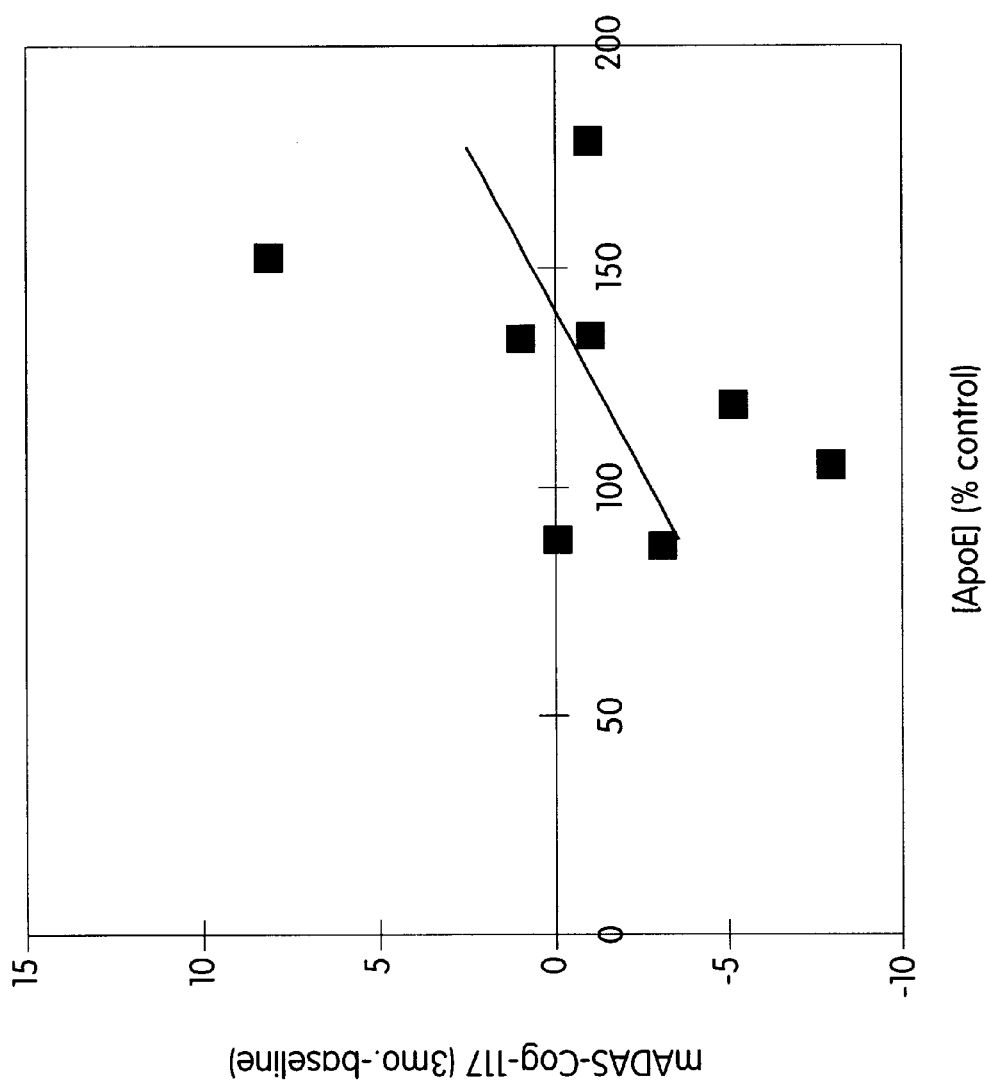
FIG. 10 is a graph representing a linear regression analysis that shows the change in ADAS-Cog scores (117 pt. extended scale) after three months as a function of change in ApoE protein levels in the CSF after 1 month ($p>0.05$; $r^2=0.20$).
Figure 11:
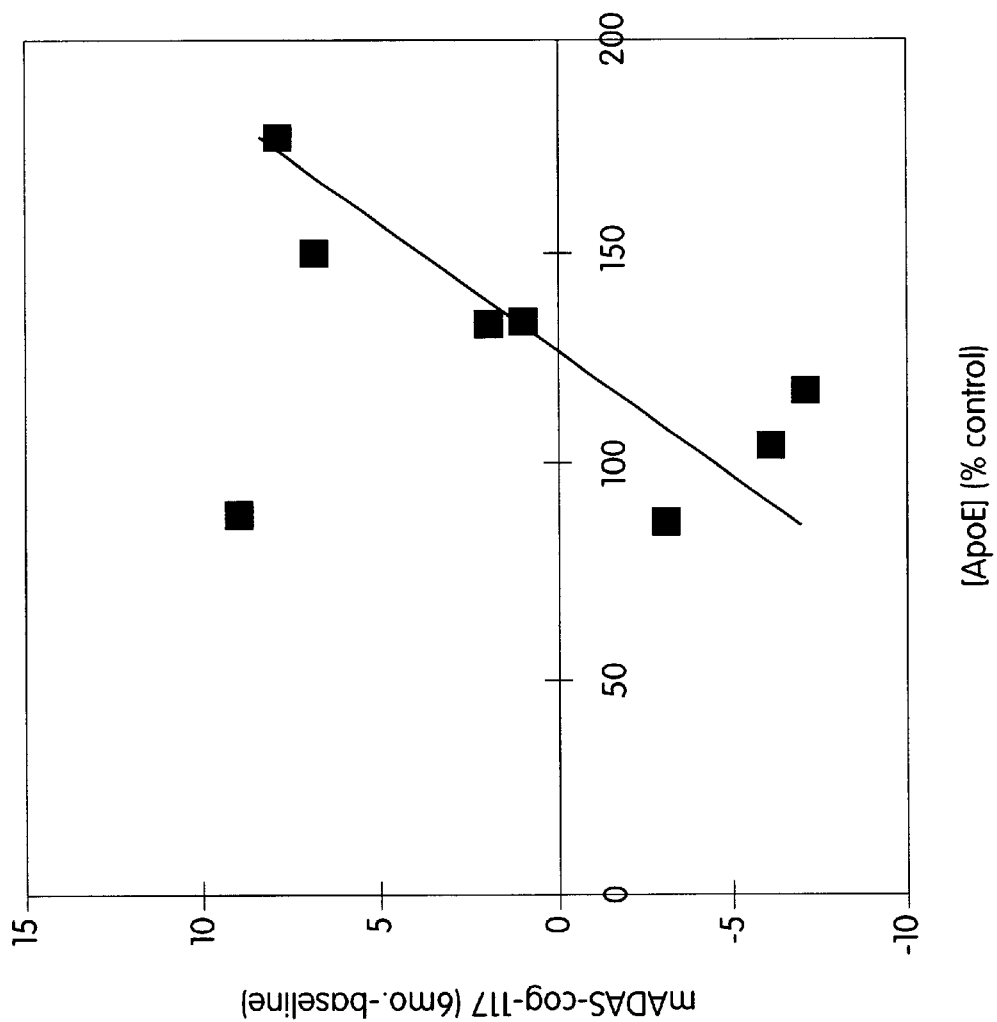
FIG. 11 is a graph representing a linear regression analysis that shows the change in ADAS-Cog scores (117 pt. extended scale)after six months as a function of change in ApoE protein levels in the CSF at one month ($p>0.05$, $r^2=0.19$; excluding patient PP 105 $p<0.02$, $r^2=0.72$).

The initial hypothesis of this study was that probucol would exert a beneficial effect on the progression of the disease by increasing the ApoE levels in the brain. FIGS. 10 and 11 summarize the changes in the ADAS-Cog scores (117 pt. extended scale) as a function of the change in ApoE protein level in the CSF.

At 3 and 6 months, there is no significant correlation between the change in ADAS-cog scores (117 pt. extended scale) and the change in ApoE protein levels in the CSF. However, if patient PP-105 is considered an outlier, a correlation ($p<0.02$) is observed at six months indicating that a higher ApoE level results in higher cognitive performance.

CIBIC-Plus

Using the Clinical Impression of Change (CIBIC-Plus) we further analyzed the effects of probucol on the cognitive function of AD patients. This test provides a holistic impression by the clinician of whether the patient has shown any change since baseline. The CIBIC is scored as a seven point scale, with a range from 1="very much improved" to 4="no change" to 7="very much worse." Changes in the CIBIC score have shown only weak correlation with changes in the ADAS-Cog and have been reported to be less sensitive to change than other measures. The FDA guidelines are widely interpreted as mandating the use of the CIBIC and this scale serves to measure the impact of treatment protocols on the quality of life for the patient.

As summarized in Table 9, the scores for the CIBIC-Plus evaluation indicate that there was a slight deterioration during the 6 month course of treatment for the group as a whole.

TABLE 9

Effect of Probucol Treatment on the Overall Impression of Change (Measured by CIBIC-Plus)

| Patient | CIBIC Scores | |
|---|---|---|
| | 3 months | 6 months |
| PP-101 | 4 | 5 |
| PP-102 | 5 | 5 |
| PP-103 | 4 | 6 |
| PP-104 | 3 | 5 |
| PP-105 | 5 | 5 |
| PP-106 | 3 | 6 |
| PP-107 | 4 | Withdrawn |
| PP-108 | 4 | 4 |
| PP-109 | 3 | 6 |
| Average | 3.9 | 5.3 |

Global Deterioration Scale

To further extend our studies on the effect of probucol on AD patient outcome, we employed the Global Deterioration Scale (GDS). The GDS test provides a description of the key features of AD progression. The GDS rates clinically identifiable stages (i.e., no cognitive decline; subjective complaints without an objective deficit; subjective complaints with some objective deficits which do not meet dementia criteria; mild dementia; moderate dementia; severe dementia; and terminal dementia). The GDS is calculated as the average of scores related to the performance in the following areas of attention and concentration, recent memory, past memory, orientation, and functioning and self care.

The results of this study as shown in Table 10, indicate that there was a relative stabilization in patient symptoms at three and six months.

TABLE 10

Results of the Global Deterioration Scale at 3 and 6 Months

| Patient | Global Deterioration Scale | | |
|---|---|---|---|
| | Baseline | 3 months | 6 months |
| PP-101 | 3.5 | 1.5 | 1 |
| PP-102 | 5 | 8 | 8 |
| PP-103 | 3 | 3.25 | 3.5 |
| PP-104 | 3.5 | 3.5 | 5.5 |
| PP-105 | 5.5 | 5 | 6.5 |
| PP-106 | 5.5 | 7 | 7 |
| PP-107 | 5.5 | 5.5 | withdrawn |
| PP-108 | 6 | 4.5 | 5 |
| PP-109 | 5 | 5 | 6 |
| Average | 4.7 | 4.8 | 5.3 |

Secondary Biochemical Markers

β-Amyloid Protein

The effects of probucol on the CSF levels of total β-amyloid protein (1–40) and (1–42) were determined after one month of treatment with probucol. Tables 11 and 12 summarize the changes in total β-amyloid protein (1–40 and 1–42) at one month, as a percentage of the baseline values.

The results indicate an overall increase in the levels of β-amyloid in the CSF of these Alzheimer's patients treated with probucol. In addition, the increase in total β-amyloid appeared to be selective for the E3/E3 genotype (Table 11). These increases in CSF β-amyloid are interesting in view of the fact that it has been reported that CSF amyloid concentration (particularly β-amyloid 1–42) decreases as the severity of the dementia increases.

TABLE 11

Changes in the CSF Concentrations of Total B.amyloid (1-40) Following One Month of Treatment with Probucol

| Patient | [β amyloid 1-40] in the CSF (average of triplicate assays) | | | |
|---|---|---|---|---|
| | Baseline | 1 month | % change | Genotype |
| PP-101 | 0.546 | 5.35 | 979 | E3/E3 |
| PP-102 | 0.100 | 2.16 | 2157 | E3/E3 |
| PP-103 | 0.996 | 3.44 | 345 | E3/E3 |
| PP-104 | 3.67 | 3.95 | 108 | E4/E3 |
| PP-105 | 4.96 | 4.96 | 100 | E3/E3 |
| PP-106 | 3.13 | 7.55 | 241 | E4/E3 |
| PP-107 | | | | |
| PP-108 | 3.10 | 3.26 | 105 | E4/E3 |
| PP-109 | 3.27 | 3.51 | 107 | E4/E3 |

TABLE 12

Changes in the CSF Concentrations of β-amyloid (1-42) Following One Month of Treatment with Probucol

| Patient | [β amyloid 1-42] in the CSF (average of triplicate assays) | | |
|---|---|---|---|
| | Baseline | 1 month | % change |
| PP-101 | 0.17 | 1.06 | 624 |
| PP-102 | 0.06 | 1.29 | 2144 |
| PP-103 | 1.02 | 2.48 | 242 |
| PP-104 | 2.76 | 3.92 | 142 |
| PP-105 | 1.35 | 0.76 | 56 |
| PP-106 | 1.25 | 1.78 | 142 |
| PP-107 | | | |
| PP-108 | 1.10 | 2.15 | 195 |
| PP-109 | ND | 0.31 | — |

Tau Protein

We summarize in Table 13 the change in Tau protein concentration in the CSF at one month relative to baseline. We observed that, as a group, there was no effect of probucol on Tau levels in this study group of Alzheimer's patients. Although probucol treatment affected the levels of ApoE and beta-amyloid in the CSF, the absence of an effect on Tau levels demonstrates the selectivity of the probucol effects.

TABLE 13

Levels of Tau Protein in the CSF at Baseline and After One Month of Treatment with Probucol

| Patient | Tau concentration in the CSF | | |
|---|---|---|---|
| | Baseline | 1 month | % change |
| PP-101 | 420 | 394 | 94 |
| PP-102 | 700 | 916 | 131 |
| PP-103 | 627 | 620 | 99 |
| PP-104 | 201 | 188 | 93 |
| PP-105 | 1012 | 1099 | 109 |
| PP-106 | 200 | 251 | 97 |
| PP-107 | 1162 | 1070 | 92 |
| PP-108 | 448 | 458 | 102 |
| PP-109 | 993 | 1120 | 113 |

EXAMPLE 11

Analysis of the Anti-Oxidant Properties of Probucol

In order to assess the antioxidant properties of probucol we analyzed lipid peroxidation levels in the CSF of patients before and after one month of treatment with probucol (one month). In vitro lipid peroxidation was measured according to the method of Oikawa et al. (*Anal. Biochem.*, 95:351–358 (1979)) with some modifications.

Briefly, cerebrospinal fluid samples from Alzheimer's disease patients were prepared in 20 volumes of phosphate buffer (pH=7) (95% $N_2$, 5% $CO_2$) with a Teflon homogenizer. After centrifligation (1000 g, 10 min., 2° C.), the supernatant was precipitated with trichloroacetic acid (72%) according to Brown et al. (*Anal. Biochem.*, 189:136–139 (1989)). This procedure removed material such as non-lipid-derived malondialdehyde (MDA) that could interfere with lipid peroxidation measurement. After precipitation with trichloracetic acid and centrifuigation (10000 g, 15 min., 2° C.), 100 μl of the supernatant containing human brain homogenates was used to measure MDA levels. These supernatants were incubated with 20 μl of SDS 10%, 150 μl of acetic acid 20% (pH 3.5), and 150 μl of thiobarbituric acid (TBA) (0.6% in 0.05 N NaOH) and heated at 100° C. for 60 min. This step was performed under a controlled atmosphere (95% N, 5% $CO^2$) in sealed vials to avoid formation of MDA during heating. At the end of the incubation, the reaction was stopped at 4° C. The MDA-TBA complex of TBARS (thiobarbituric acid reactive substances) was then extracted with 300 μl of butanolipyridine (15:1) by strong shaking (for 30 sec.) followed by centrifugation (1000 g, 10 min., 4° C.). TBARS present in the organic phase was than measured in a Perkin-Elmer spectrofluorophotometer (connected to a microplate reader (96 wells) with λ excitation of 532 nm and λ emission at 553 nm) and results are reported in Table 14.

TABLE 14

Change in Lipid Peroxidation After Treatment with Probucol

| Patient | Lipid Peroxidation (Fluorescence Units) | | Change (% baseline) |
|---|---|---|---|
| | baseline | 1 month | |
| PPI-101 | 0.745 | 0.691 | 92.8 |
| PPI-102 | 0.704 | 0.731 | 103.8 |
| PPI-103 | 0.710 | 0.824 | 116.1 |
| PPI-104 | 0.703 | 0.705 | 100.3 |
| PPI-105 | 0.704 | 0.686 | 97.4 |
| PPI-106 | 0.725 | 0.687 | 94.8 |
| PPI-107 | | | |
| PPI-108 | 0.710 | 0.692 | 97.5 |
| PPI-109 | 0.714 | 0.744 | 104.2 |
| Change (% Baseline) | | | 100.9 |

Each value is the average of 4–6 separate determinations

After 1 month of dosing with probucol, the average for eight patients indicated no changes in the levels of lipid peroxidation in the CSF relative to baseline values. For individual patients, any changes in lipid peroxidation (higher or lower) were small.

Figure 12:
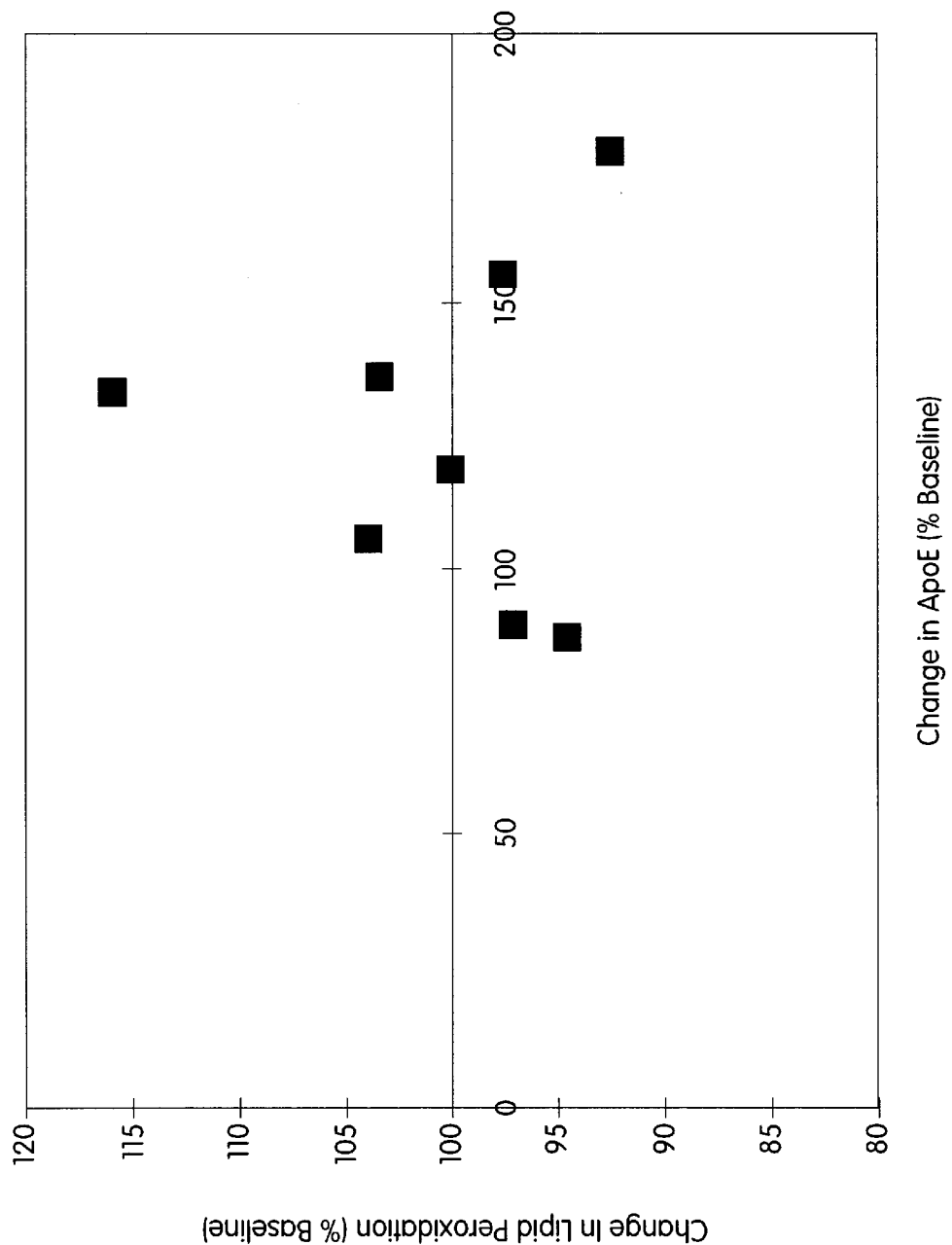
FIG. 12 is a graph representing a linear regression analysis that depicts the relationship between the change in lipid peroxidation (% baseline) as a function of a change in ApoE levels.
Figure 13:
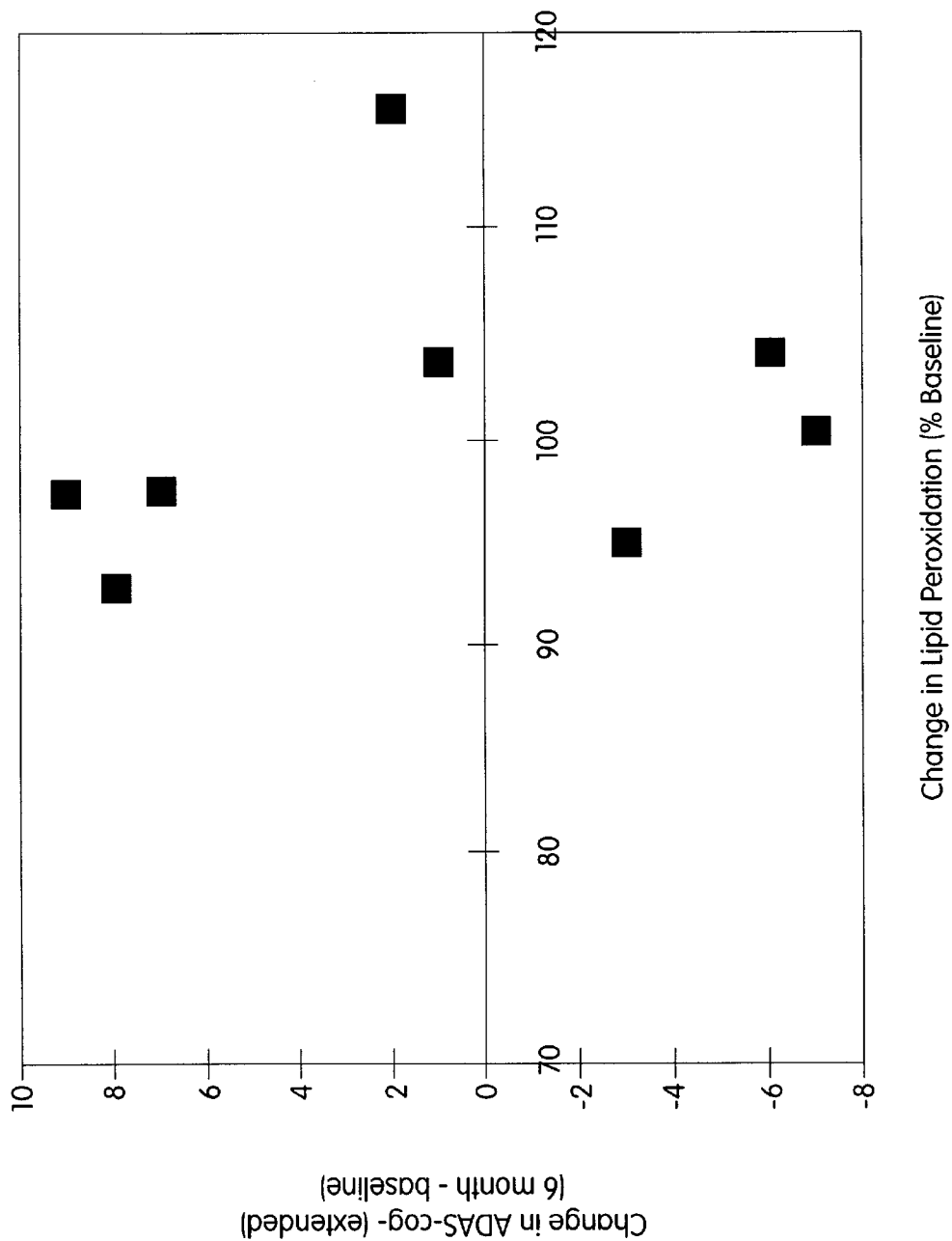
FIG. 13 is a graph representing a linear regression analysis that depicts the relationship between the change in ADAS-Cog scores (117 pt. extended scale; six months—baseline) as a function of change in lipid peroxidation (% baseline).
Figure 14:
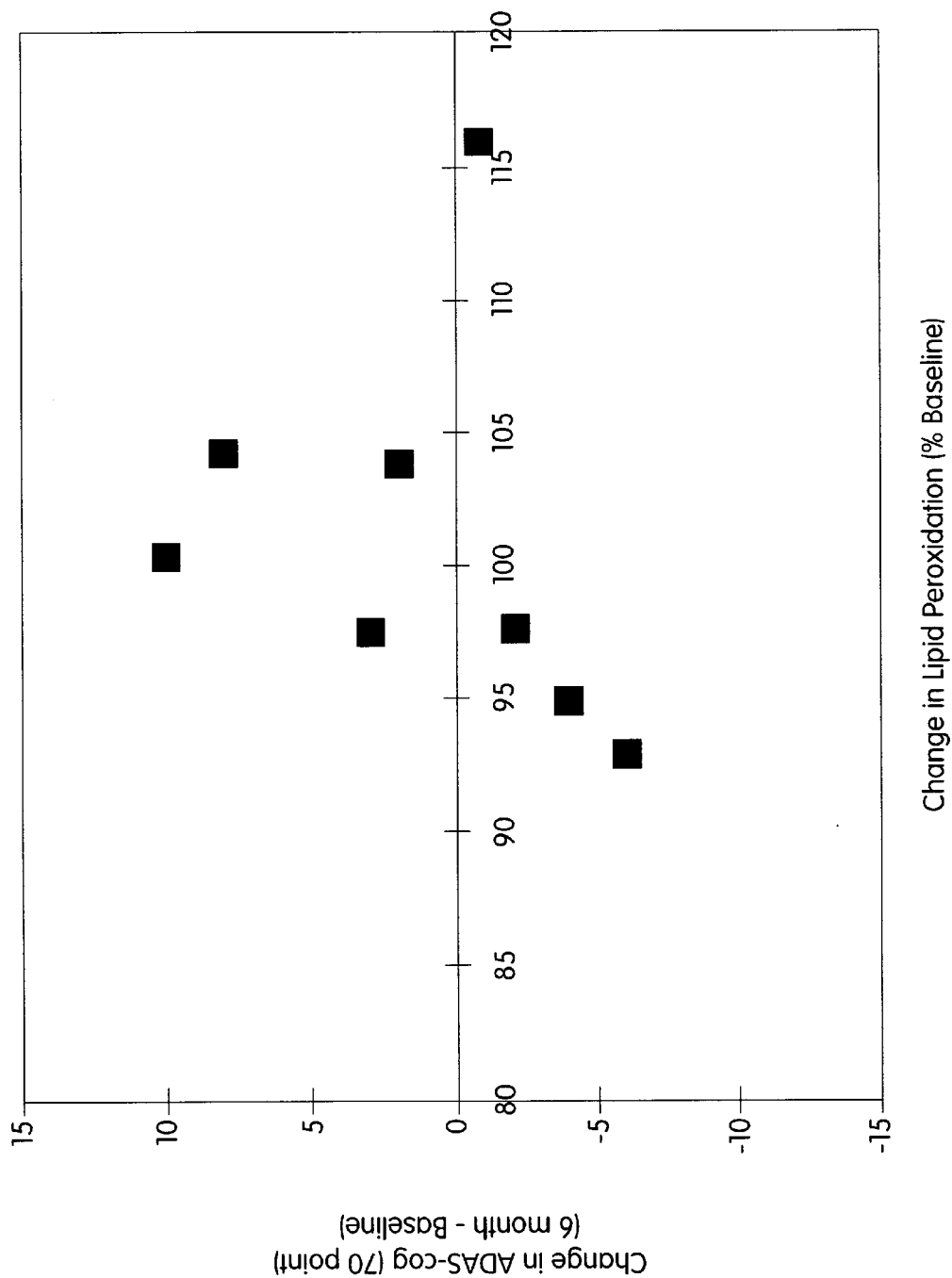
FIG. 14 is a graph representing a linear regression analysis that depicts the relationship between the change in ADAS-Cog scores (70 pt. scale; six months—baseline) as a function of change in lipid peroxidation (% baseline).

In addition to the relationship between probucol and lipid peroxidation, we wanted to determine if the antioxidant properties of probucol had any effect on ApoE levels and AD patient outcome. We performed a linear regression analysis curve that examined the relationship between the change in lipid peroxidation (% baseline) as a function of a change in ApoE levels (FIG. 12). We also performed a similar analysis that examined the relationship between the change in ADAS-Cog scores (70 pt. and 117 pt.; six months—baseline) as a function of any change in lipid peroxidation levels (FIGS. 13 and 14).

As shown in FIG. 12, we observed no correlation between changes in lipid peroxidation and ApoE induction. Similarly, as shown in FIGS. 13 and 14, no correlation between changes in individual ADAS-Cog scores (70 pt or 117 pt) and changes in lipid peroxidation were observed. Thus, although our study group was small, we concluded that probucol exerts its pharmacologic effect primarily through mechanisms related to ApoE induction.

EXAMPLE 12

Animal Models for Determining the Efficacy of Probucol in Treating Stroke

To demonstrate if increasing ApoE levels with probucol provides a neuroprotective effect in treating stroke, several animal models known in the art may be employed (e.g., Simpkins et al., *J Neurosurg.* 87(5):724–730 (1997); Nawashiro et al., *J. Cereb. Blood Flow Metab.* 17(5) 483–490 (1997); and Connolly et al., *Neurosurgery* 38(3): 523–531 (1996)).

In particular, the Wistar rat model may be used with modifications. Briefly, rats are dosed (i.p.) daily with probucol or a saline negative control for ten days. On the tenth day, animals are then subjected to a 2 hour reversible, middle cerebral artery occlusion. Laser-Doppler flowmetry is used to monitor the ischemic period and early reperfusion. After 22 hours of reperfusion, the infarct volume is then determined by 0-2,3,5-triphenyltetrazolium chloride staining and image analysis.

We predict that the cortical infarct volumes (indicative of neuronal damage) will be less in animals treated with probucol as compared to untreated animals.

To extend these animal studies, the ApoE knockout mouse may be exploited to assess the role of ApoE in probucol-mediated neuroprotection for stroke. This model will permit the evaluation of probucol in animals where ApoE can be induced (wild type) or is non-existent due to an apoE gene disruption.

This protocol is carried out as similarly described for the rat model above, with some modifications. Briefly, mice (wild type or ApoE-knockout) are dosed (i.p.) daily with probucol (5 mg) or a saline negative control for ten days. On the tenth day, animals are subjected to a transient focal ischemia by intraluminal occlusion of the middle cerebral artery. Infarct volume, neurological outcome, and cerebral flow will be monitored. Our prediction is that treatment with probucol would be expected to have little or no benefit in the knockout animals if ApoE induction is necessary for the neuroprotective properties of probucol in treating stroke.

It will be appreciated that these protocols may be modified to also determine the effect of probucol in treating sudden acute stroke in an animal (probucol administered after the induced ischemic incident). In addition, the above stroke model may be employed using larger mammals (e.g., cats, dogs) for formulating preclinical dosage ranges, methods of administration, or other parameters in preparation for carrying out a human clinical trial.

Other Embodiments

Preferably, compositions containing probucol (Lorelco™ manufactured by Marion Merrell Dow Inc.), tacrine (Cognex™, manufactured by Parke-Davis), heptylphysostigmine (manufactured by Merck Corp.), Simvastatin (Zocor™, manufactured by Merck Corp.), lovastatin (Mevacori, manufactured by Merck Corp.), pravastatin (Pravachol™, manufactured by Bristol-Myers Squibb), thorvastatin (Parke-Davis), probucol analogs, vitamin E, donepezil (Aricept™, marketed by Pfizer), blood pressure inhibitors, antioxidants, anti-inflammatories, and steroids are suitable for altering ApoE as described herein and useful for the treatment of human patients, but these compounds may also be used to treat any other mammal, for example, any pet or domesticated livestock. Any neurodegenerative problems associated with the types of altered brain function described herein may be improved with any of the compositions described above.

In addition, normal nervous system biology may also be enhanced by the administration of compositions described herein with improvements in cognitive performance or other nervous system performance being the result.

For any of these additional uses, these compositions as described above are administered by the general methods described herein.

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

Other embodiments are within the claims.

What is claimed is:

1. A method of treating a neuronal deficit in a patient, said patient diagnosed with Alzheimer's disease or having a predisposition to Alzheimer's disease, said method comprising administering a therapeutically-effective amount of a composition comprising probucol or an analog of probucol, said composition being a composition which increases ApoE levels.

2. The method of claim 1, wherein said method further comprises administering a second compound, said second compound comprising probucol analogs, vitamin E, donepezil, blood pressure inhibitors, antioxidants, anti-inflammatories, or steroids other Than estrogen.

3. The method of claim 1, wherein said therapeutically effective amount of a composition is sufficient to increase ApoE levels by about 10% or more.

4. The method of claim 1, wherein said therapeutically effective amount of a composition is sufficient to increase amyloid scavenging by ApoE.

5. The method of claim 1, wherein said patient is presymptomatic.

6. The method of claim 1, wherein said patient has at least one apoE4 allele.

7. The method of claim 1, wherein said administering further includes administering tacrine to said patient.

8. The method of claim 1, wherein said administering further includes administering estrogen to said patient.

9. The method of claim 1, wherein said administering further includes administering donepezil to said patient.

10. A method of increasing ApoE polypeptide levels in a patient diagnosed with Alzheimer's disease or having a pedisposition to Alzheimer's disease, said method comprising administering a therapeutically-effective amount of a composition comprising probucol or an analog of probucol.

11. The method of claim 10, wherein said patient has at least one apoE4 allele.

12. The method of claim 10, wherein said composition further comprises a compound comprising probucol analogs, tacrine, heptylphysostigmine, simvastatin, lovastatin, pravastatin, thorvastatin, vitamin E, donepezil, blood pressure inhibitors, antioxidants, anti-inflammatories, or steroids.

13. The method of claim 10 wherein said composition further includes one or more compounds comprising, vitamin E, donepezil, blood pressure inhibitors, antioxidants, anti-inflammatories, or steroids.

14. The method of claim 10, wherein said ApoE polypeptide levels are measured by quantitating ApoF polypeptide levels.

15. The method of claim 10, wherein said ApoE polypeptide levels are measured by quantitating ApoE polypeptide levels with an antibody.

16. The method of claim 10, wherein said increasing is in brain tissue or human cerebrospinal fluid of said patient.

* * * * *